(12) United States Patent
Radmand et al.

(10) Patent No.: US 12,048,646 B2
(45) Date of Patent: Jul. 30, 2024

(54) JIG ASSEMBLY FOR POSITIONING TEETH OF A PATIENT

(71) Applicant: Achaemenid, LLC, Boston, MA (US)

(72) Inventors: Reza Radmand, Boston, MA (US); Stephen J Cole, White Plains, NY (US)

(73) Assignee: Achaemenid, LLC, Boston, MA (US)

( * ) Notice: Subject to any disclaimer, the term of this patent is extended or adjusted under 35 U.S.C. 154(b) by 402 days.

(21) Appl. No.: 17/321,597

(22) Filed: May 17, 2021

(65) Prior Publication Data

US 2021/0267789 A1 Sep. 2, 2021

Related U.S. Application Data

(63) Continuation of application No. 16/871,477, filed on May 11, 2020, which is a continuation-in-part of application No. PCT/US2018/060066, filed on Nov. 9, 2018.

(60) Provisional application No. 62/889,383, filed on Aug. 20, 2019, provisional application No. 62/689,380, filed on Jun. 25, 2018, provisional application No. 62/678,287, filed on May 31, 2018, provisional application No. 62/678,292, filed on May 31, 2018, provisional application No. 62/595,712, filed on Dec.
(Continued)

(51) Int. Cl.
*A61F 5/56* (2006.01)
(52) U.S. Cl.
CPC .................................. *A61F 5/566* (2013.01)

(58) Field of Classification Search
CPC ...... A61F 5/56; A61F 5/566; A61F 2005/563; A63B 71/085; A63B 2071/086; A63B 2071/088; A61C 7/08; A61C 7/36
See application file for complete search history.

(56) References Cited

U.S. PATENT DOCUMENTS 4,238,188 A 12/1980 Armstrong
4,856,991 A 8/1989 Breads et al.
(Continued)

FOREIGN PATENT DOCUMENTS

DE 202005006171 U1 9/2005
EP 2491901 B1 7/2014
(Continued)

OTHER PUBLICATIONS

United States Patent and Trademark Office; Non-Final Office Action for U.S. Appl. No. 16/871,477; dated Jul. 8, 2022; 28 pages.
(Continued)

*Primary Examiner* — Camtu T Nguyen
(74) *Attorney, Agent, or Firm* — Womble Bond Dickinson (US) LLP

(57) ABSTRACT

A jig assembly may include an upper jig including an upper bite block for receiving upper teeth, a lower jig including a lower bite block for receiving lower teeth, and a fastener for securing each of the upper jig and the lower jig in a fixed position relative to one another. A jig assembly may include a first jig and a second jig coupled to the first jig. The first jig and the second jig may be switchable between a first configuration in which the first jig is slidable relative to the second jig in a first direction and a second configuration in which the first jig and the second jig are fixed relative to each other in the first direction.

20 Claims, 21 Drawing Sheets

Related U.S. Application Data 7, 2017, provisional application No. 62/592,857, filed on Nov. 30, 2017, provisional application No. 62/585,145, filed on Nov. 13, 2017.

(56) References Cited

U.S. PATENT DOCUMENTS

| | | | |
|---|---|---|---|
| 5,154,609 A * | 10/1992 | George | A61C 9/0006 433/68 |
| 5,570,704 A | 11/1996 | Buzzard et al. | |
| 6,055,986 A | 5/2000 | Meade | |
| 7,077,646 B2 | 7/2006 | Hilliard | |
| 7,448,388 B2 | 11/2008 | Halstrom | |
| 7,832,403 B2 * | 11/2010 | Halstrom | A61F 5/566 128/848 |
| 8,123,521 B1 * | 2/2012 | Kopp | A61C 9/0006 433/68 |
| 8,226,407 B2 | 7/2012 | Hanewinkel et al. | |
| D685,098 S | 6/2013 | Tompkins | |
| 8,684,006 B2 | 4/2014 | Levendowski et al. | |
| 8,783,259 B2 | 7/2014 | Spencer | |
| D720,858 S | 1/2015 | Burlon | |
| D777,930 S | 1/2017 | Raad | |
| D777,931 S | 1/2017 | Raad | |
| 9,615,964 B2 | 4/2017 | Rogers | |
| D802,145 S | 11/2017 | Voudouris | |
| 9,949,867 B2 | 4/2018 | Veis et al. | |
| D827,835 S | 9/2018 | Bocala | |
| D848,001 S | 5/2019 | Buddemeyer et al. | |
| 10,583,031 B2 | 3/2020 | Quaka et al. | |
| 10,881,547 B2 | 1/2021 | Metz | |
| D950,066 S | 4/2022 | Yukita et al. | |
| 2005/0016547 A1 | 1/2005 | Mousselon et al. | |
| 2005/0028827 A1 * | 2/2005 | Halstrom | A61F 5/566 128/848 |
| 2005/0175954 A1 * | 8/2005 | Zacher | A61F 5/566 433/5 |
| 2008/0099029 A1 | 5/2008 | Amberg | |
| 2011/0155144 A1 | 6/2011 | Tousssaint | |
| 2012/0145166 A1 | 6/2012 | Fallon et al. | |
| 2013/0074848 A1 | 3/2013 | Metz | |
| 2015/0101614 A1 | 4/2015 | Quaka et al. | |
| 2016/0022474 A1 | 1/2016 | Magness | |
| 2016/0199215 A1 | 7/2016 | Kopelman | |
| 2016/0199216 A1 | 7/2016 | Cam et al. | |
| 2017/0007363 A1 | 1/2017 | Boronkay | |
| 2017/0151086 A1 | 6/2017 | Fareid | |
| 2017/0367793 A1 | 12/2017 | Veis | |
| 2018/0000563 A1 | 1/2018 | Shanjani et al. | |
| 2018/0000629 A1 | 1/2018 | Remmers et al. | |
| 2018/0078343 A1 | 3/2018 | Falkel | |
| 2019/0110866 A1 | 4/2019 | Nagai et al. | |
| 2019/0125574 A1 | 5/2019 | Ignacio et al. | |
| 2020/0046466 A1 | 2/2020 | Yukita et al. | |
| 2020/0405527 A1 | 12/2020 | Remmers et al. | |

FOREIGN PATENT DOCUMENTS

| | | |
|---|---|---|
| KR | 102001772 B1 | 7/2019 |
| WO | 2015104683 A2 | 7/2015 |
| WO | 2017095971 A1 | 6/2017 |

OTHER PUBLICATIONS

United States Patent and Trademark Office; Requirement for Restriction/Election for U.S. Appl. No. 16/871,477; dated Jan. 18, 2022; 8 pages.

European Patent Office; Supplementary European Search Report for EP Application No. 18876255.3; dated Sep. 23, 2021; 10 pages.

United States Patent and Trademark Office; Final Office Action for U.S. Appl. No. 16/871,477; dated Feb. 17, 2023; 29 pages.

United States Patent and Trademark Office; Notice of Allowance for U.S. Appl. No. 29/786,095; dated Mar. 31, 2023; 5 pages.

Dentistry IQ, How to Treat Invisalign patients for sleep-disordered breathing, Sep. 21, 2015, 4 pgs., https://www.dentistryiq.com/.

Moira Wong Orthodontics, Advanced Braces for Children, Sep. 5, 2017, 7 pgs., https://moirawongorthodontics.co.uk/advanced-braces-children/.

Sacramento Dentistry Group, Using Invisalign with Oral Appliance Therapy, Jan. 25, 2018, 3 pgs., https://www.sacramentodentistry.com/.

Dr. Sylvain Chamberland Orthodontiste, Mandibular advancement device, Nov. 3, 2013, 9 pgs., https://www.sylvainchamberland.com/en/ortho-101-en/mandibular-advancement-device/.

Sleeparchitx, The Aligner Sleep Appliance System, Oct. 6, 2017, 2 pgs., https://sleeparchitx.com/alignersleepappliance.html.

International Searching Authority, International Search Report and Written Opinion of International App. No. PCT/US2018/060066, dated Mar. 5, 2019, 19 pgs.

Dental Care, Sleep Apnea Management for the Dentist, Dental Impressions and Bite Registration, Sep. 30, 2020, 3 pgs. https://www.dentalcare.com/en-us/professional-education/ce-courses/ce578/dental-impressions-and-bite-registration.

Dream Systems Dental Lab, George Gauge Bite Technique, Nov. 25, 2020, 2 pgs., http://www.dreamsystemsdentallab.com/wp-content/uploads/2016/04/GeorgeGaugeBiteTechnique-9.pdf.

EPO, Communication pursuant to Rules 161(2) and 162 EPC, EP Application No. 18876255.3-1126, dated Oct. 2, 2020, 3 pgs.

CA Office Action dated Feb. 15, 2024 for related CA Application No. 3, 117,315, filed Apr. 21, 2021; 4 pages.

European Patent Office; Communication under Rule 71(3) EPC "Intention to Grant" issued in European Application No. 18876255.3 dated Jun. 26, 2023, 48 pages.

* cited by examiner

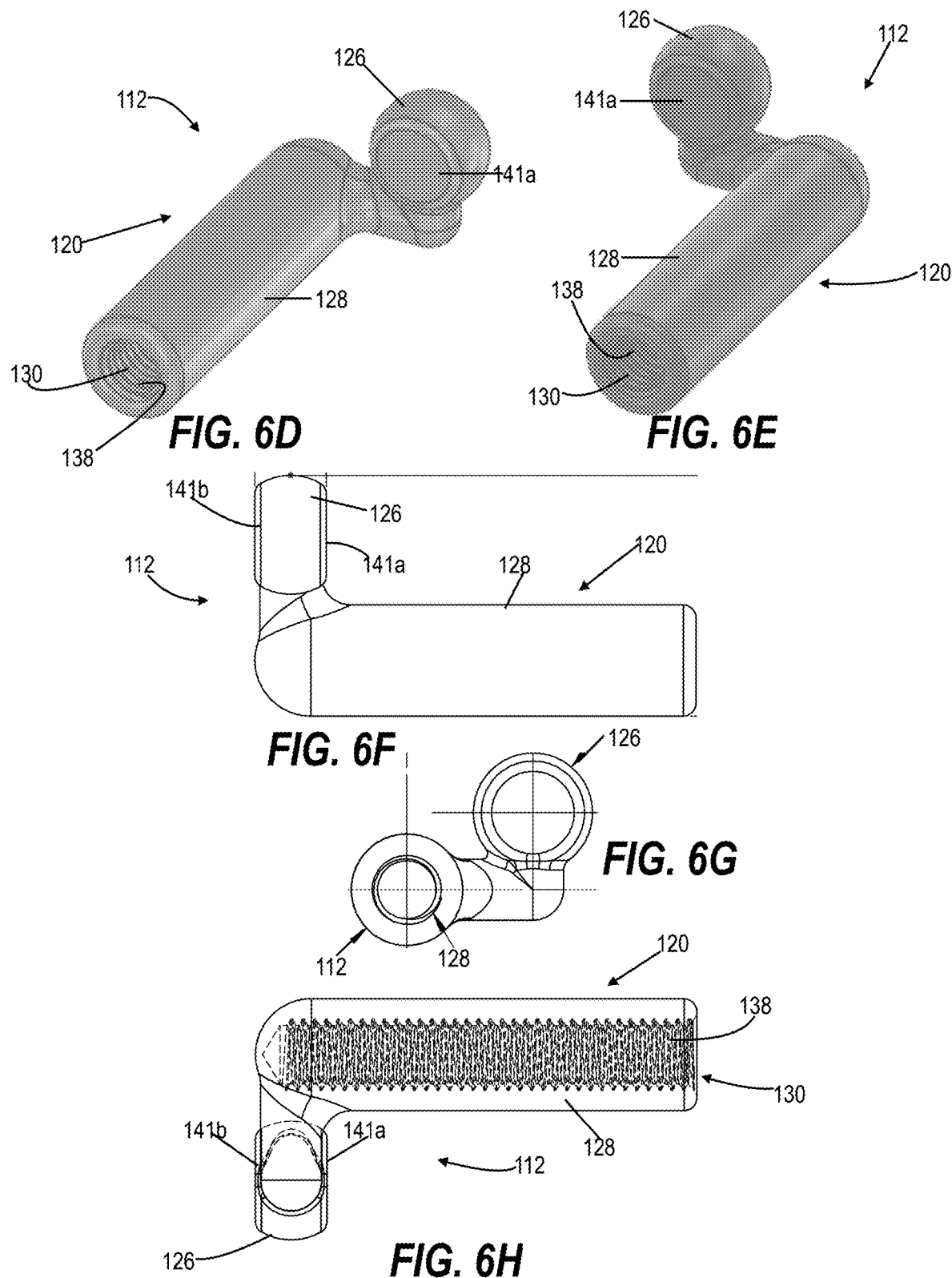

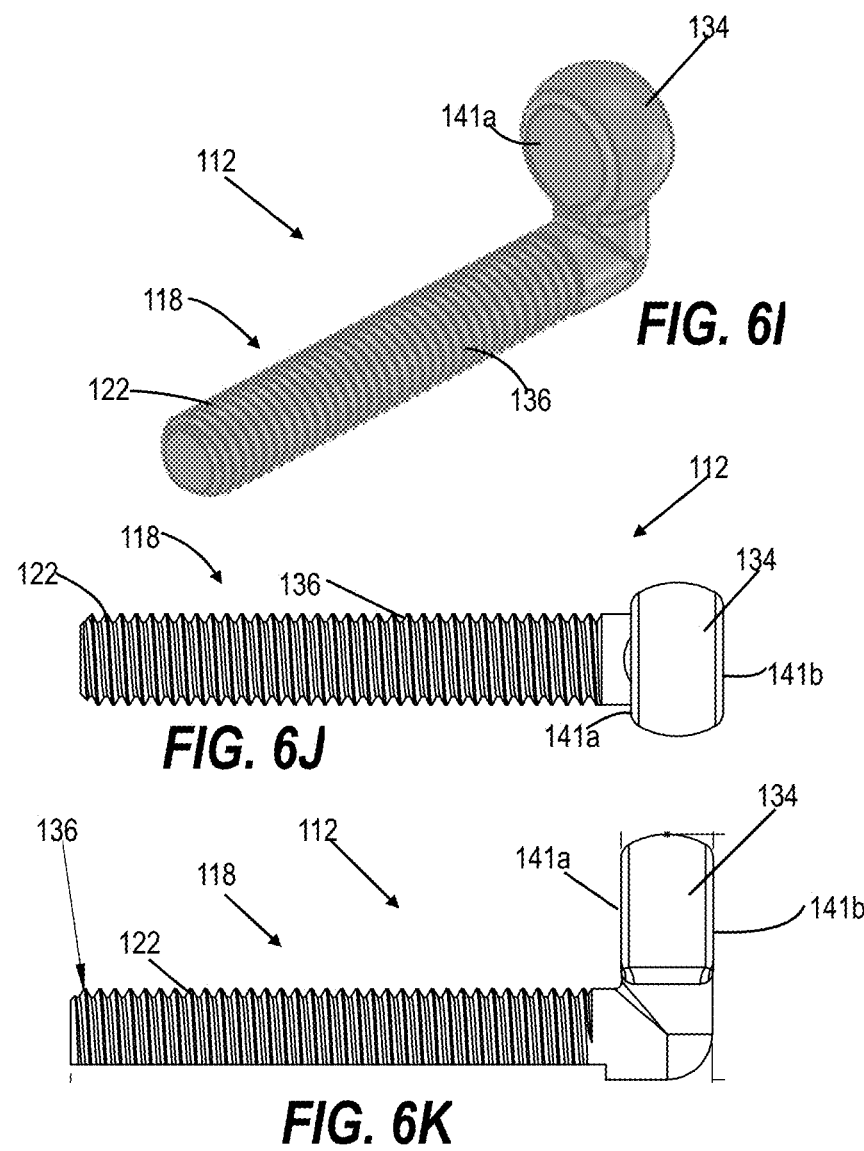

JIG ASSEMBLY FOR POSITIONING TEETH OF A PATIENT

CROSS-REFERENCE TO RELATED APPLICATIONS

This application is a continuation of U.S. application Ser. No. 16/871,477 filed May 11, 2020, which is a Continuation-in-Part of International Application No. PCT/US2018/060066 filed Nov. 9, 2018, which claims the benefit of U.S. Provisional Patent Application No. 62/585,145, filed Nov. 13, 2017, U.S. Provisional Patent Application No. 62/592,857, filed Nov. 30, 2017, U.S. Provisional Patent Application No. 62/595,712, filed Dec. 7, 2017, U.S. Provisional Patent Application No. 62/678,287, filed May 31, 2018, U.S. Provisional Patent Application No. 62/678,292, filed May 31, 2018, and U.S. Provisional Patent Application No. 62/689,380, filed Jun. 25, 2018, each of which is incorporated herein by reference in its entirety. U.S. application Ser. No. 16/817,477 claims the benefit of U.S. Provisional Patent Application No. 62/889,383 filed Aug. 20, 2019, which is incorporated herein by reference in its entirety.

FIELD OF THE DISCLOSURE

A provisional oral sleep appliance and a method for providing temporary treatment of obstructive sleep apnea in a user is described. A jig or jig assembly for positioning the upper and lower jaws relative to one another, and optionally obtaining images and/or impressions of a patient's teeth and/or gums and, for example, for making an oral sleep appliance, is also described. The use of an oral sleep appliance with an orthodontic aligner is also contemplated.

BACKGROUND OF THE DISCLOSURE

Sleep apnea is a common medical condition during which a person experiences one or more pauses in breathing and/or shallow breaths during sleep. While there are several types of sleep apnea, the most common type is obstructive sleep apnea. In this medical condition, one or more of the person's throat muscles relax during sleep causing surrounding tissues in the posterior portions of the mouth, nose and throat to collapse and block the airway. Persons suffering from obstructive sleep apnea have inadequate oxygen exchange during sleep, which can lead to daytime fatigue, lack of concentration and mood changes. Left untreated, obstructive sleep apnea can have a significant impact on a person's health, often leading to cardiovascular, stroke and metabolic disorders.

Known methods for treatment of obstructive sleep apnea include both surgical methods or interventions and nonsurgical devices. A popular surgical procedure is uvulopalatopharyngoplasty, whereby a portion of the soft palate is removed in an effort to prevent closure of the airway by excess tissue during sleep. A disadvantage of this procedure, however, is that the operation is often expensive and may damage throat muscles necessary for swallowing and/or cause other undesirable disorders, such as, nasal regurgitation. To reduce this risk, various nonsurgical approaches have been employed. Once such nonsurgical approach includes using standardized oral appliances to incrementally advance and/or protrude the mandible (lower jaw) relative to the maxilla (upper jaw). These standardized appliances, commonly referred to as mandibular advancement devices ("MADs"), typically include upper and lower dental trays, in which the lower dental tray is designed to advance the mandible, and hence, move the tongue forward to increase the space in the posterior part of the throat and the oropharynx, which in turn may serve to increase the flow of air during sleep. The distance (degree of advancement) required to protrude and/or reposition the mandible may be, at least in part, dependent on the severity of the individual's obstructive sleep apnea, as well as psychological variables among the users.

Once a patient is diagnosed with sleep apnea, a permanent MAD may be made. To do so, the dentist may take a three-dimensional scan of the patient's teeth and gums, and/or may obtain oral impressions of the patient's teeth and gums. Accordingly, there is a need for devices and methods that facilitate obtaining a scan and/or impression of the patient's teeth and gums for use in fabricating a MAD or other oral appliance. There is also a need for a relatively simple, cost-effective, temporary means of providing apneic relief to a patient while waiting for a permanent oral appliance to be made. There is further a need to be able to treat sleep apnea while a patient is also undergoing orthodontic alignment treatment.

BRIEF DESCRIPTION OF THE EXEMPLARY EMBODIMENTS

An exemplary embodiment of a jig assembly may include an upper jig including an upper bite block for receiving upper teeth, a lower jig including a lower bite block for receiving lower teeth, and a fastener for securing each of the upper jig and the lower jig in a fixed position relative to one another.

An exemplary embodiment of a jig assembly may include a first jig and a second jig coupled to the first jig. The first jig and the second jig may be switchable between a first configuration in which the first jig is slidable relative to the second jig in a first direction and a second configuration in which the first jig and the second jig are fixed relative to each other in the first direction.

BRIEF DESCRIPTION OF THE DRAWINGS

A more particular description will be rendered by reference to specific embodiments thereof that are illustrated in the appended drawings. Understanding that these drawings depict only typical embodiments thereof and are not therefore to be considered to be limiting of its scope, exemplary embodiments will be described and explained with additional specificity and detail through the use of the accompanying drawings in which:

FIG. 6D is a perspective view of a cylinder for use with the strut assembly of FIG. 6C;

FIG. 6E is a perspective view of a cylinder for use with the strut assembly of FIG. 6C;

FIG. 6F is a side view of a cylinder for use with the strut assembly of FIG. 6C;

FIG. 6G is a bottom view of a cylinder for use with the strut assembly of FIG. 6C;

FIG. 6H is a cross-sectional view of a cylinder for use with the strut assembly of FIG. 6C;

FIG. 6I is a perspective view of a rod for use with the strut assembly of FIG. 6C;

FIG. 6J is a right-side view of a rod for use with the strut assembly of FIG. 6C;

FIG. 6K is a side view of a rod for use with the strut assembly of FIG. 6C;

Figure 1A:
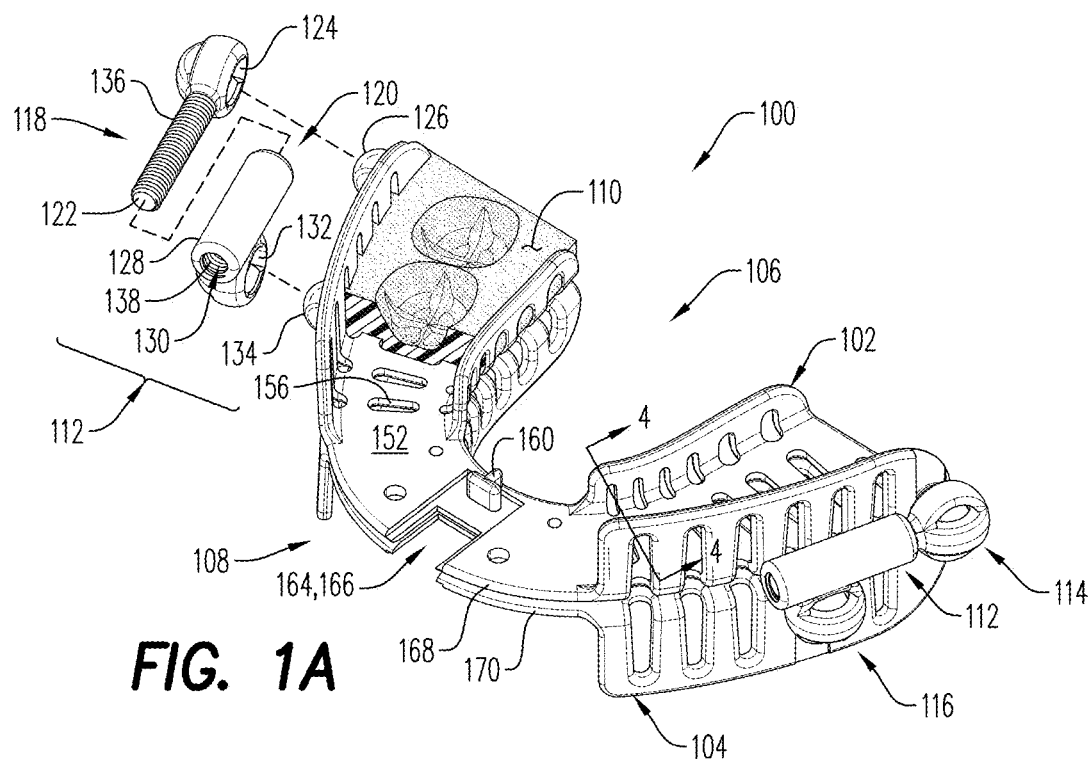
FIG. 1A is a schematic, partially exploded view of an exemplary provisional oral appliance according to an embodiment.

Various features, aspects, and advantages of the embodiments will become more apparent from the following detailed description, along with the accompanying figures in which like numerals represent like components throughout the figures and text. The various described features are not necessarily drawn to scale, but are drawn to emphasize specific features relevant to some embodiments.

The headings used herein are for organizational purposes only and are not meant to limit the scope of the description or the claims. To facilitate understanding, reference numerals have been used, where possible, to designate like elements common to the figures.

DETAILED DESCRIPTION

For purposes of illustrating features of the embodiments, an example will now be introduced and referenced throughout the disclosure. Those skilled in the art will recognize that this example is illustrative and not limiting and is provided purely for explanatory purposes.

Figure 6A:
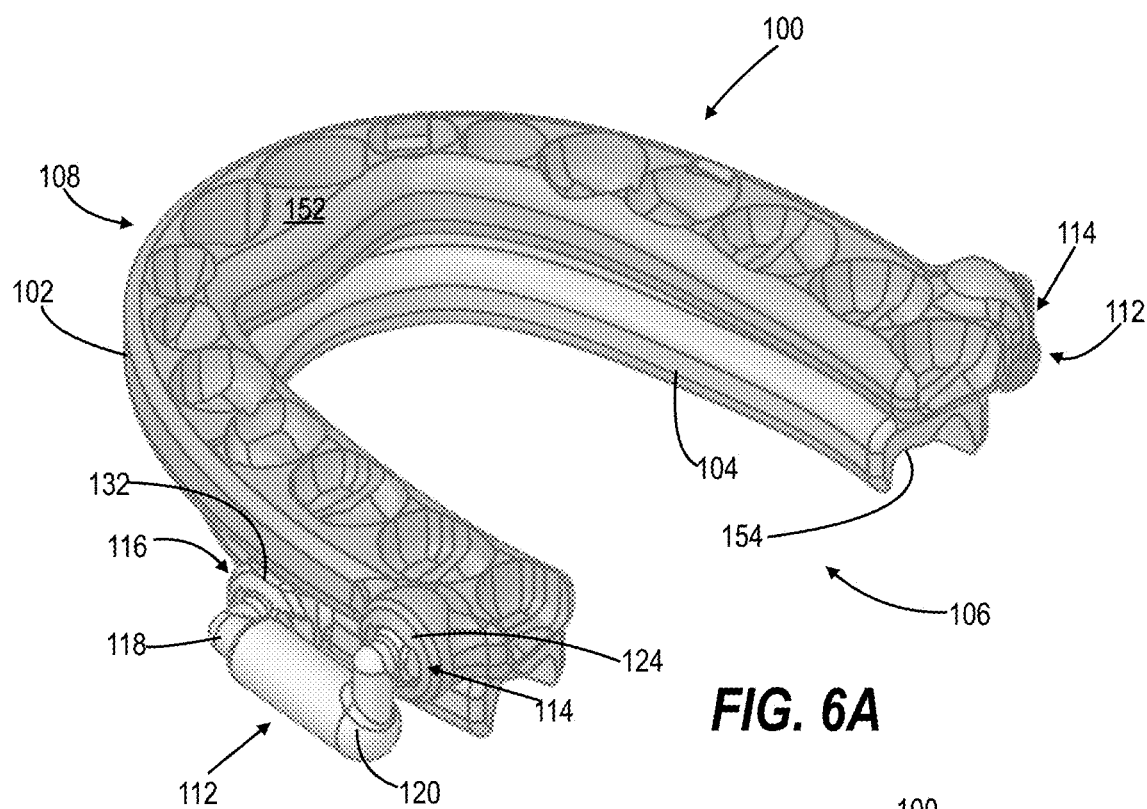
FIG. 6A is a perspective view of an exemplary provisional oral appliance according to an embodiment.
Figure 6B:
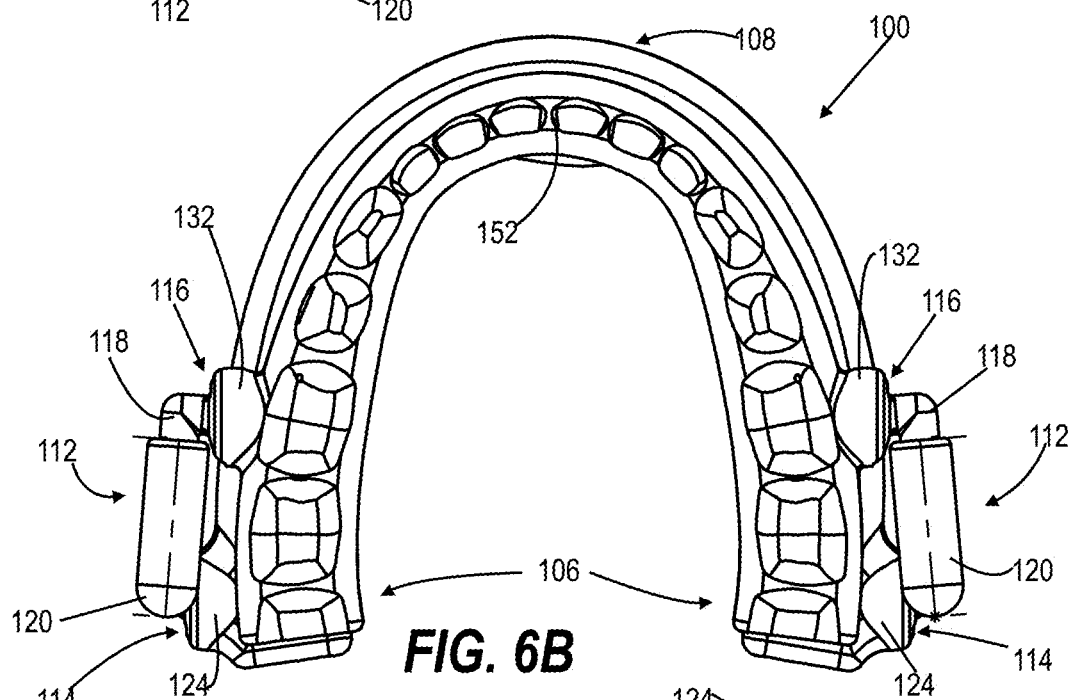
FIG. 6B is a top view of the provisional oral appliance of FIG. 6A.

In one aspect, this disclosure is directed to a provisional (i.e., transitional) oral appliance for the temporary treatment of sleep apnea. For example, FIG. 1A, FIG. 6A and FIG. 6B each illustrates an exemplary provisional oral appliance (sometimes simply referred herein to as "oral appliance" or "appliance") 100. The appliance 100 includes a first (i.e., upper) plate/tray 102 and a second (i.e., lower) plate/tray 104 in an opposed, facing relationship with one another. The upper tray 102 and lower tray 104 each include a respective posterior end (or portion) along a posterior end (or portion) 106 of the appliance 100 and an anterior end (or portion) along an anterior end (or portion) 108 of the appliance 100. The first tray 102 and the second tray 104 may be provided in various standard/generic sizes (similar to sports mouth guards), such as small, medium, large, or extra-large. The selected size may be based on the individual patient's jaw size, which helps to provide for a comfortable fit to the patient's dentition (i.e., configuration of teeth and gums). As will be understood by those of skill in the art, the appliance 100 is intended to be worn on the teeth of a user, such that the upper tray 102 receives the upper teeth of the user and the lower tray 104 receives the lower teeth of the user. Accordingly, at least a portion of at least one of the upper and lower trays 102, 104 may be filled with a polymeric material (e.g., a cured reline material) 110 (shown only along a portion of the upper tray 102 in FIG. 1A) that conforms to the patient's teeth. FIGS. 6A and 6B each illustrate the first tray 102 being conformed to a patient's teeth. It is contemplated that this ensures a comfortable and secure fit for the patient.

Figure 6C:
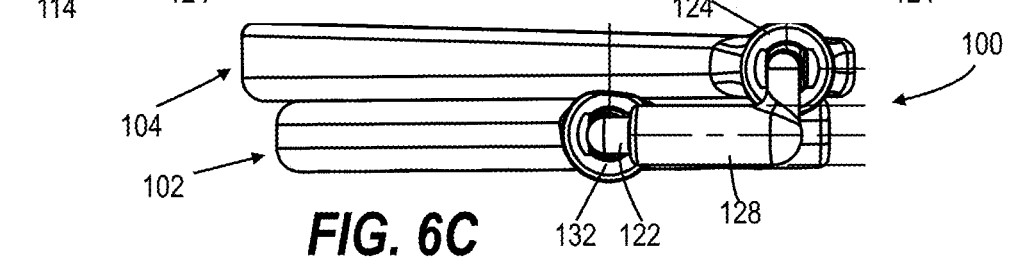
FIG. 6C is a side view of the provisional oral appliance of FIG. 6A, illustrating a strut assembly, according to an aspect.
Figure 7:
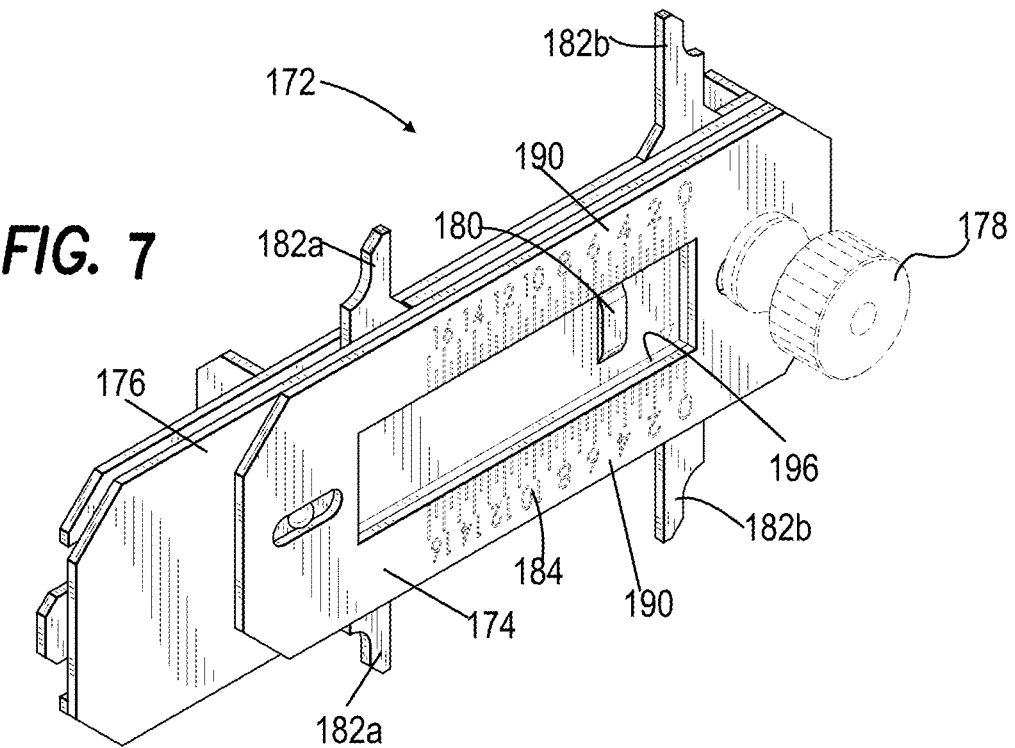
FIG. 7 is a top front perspective view of a length gauge that may be used to measure the length of a strut assembly, according to an embodiment.
Figure 8:
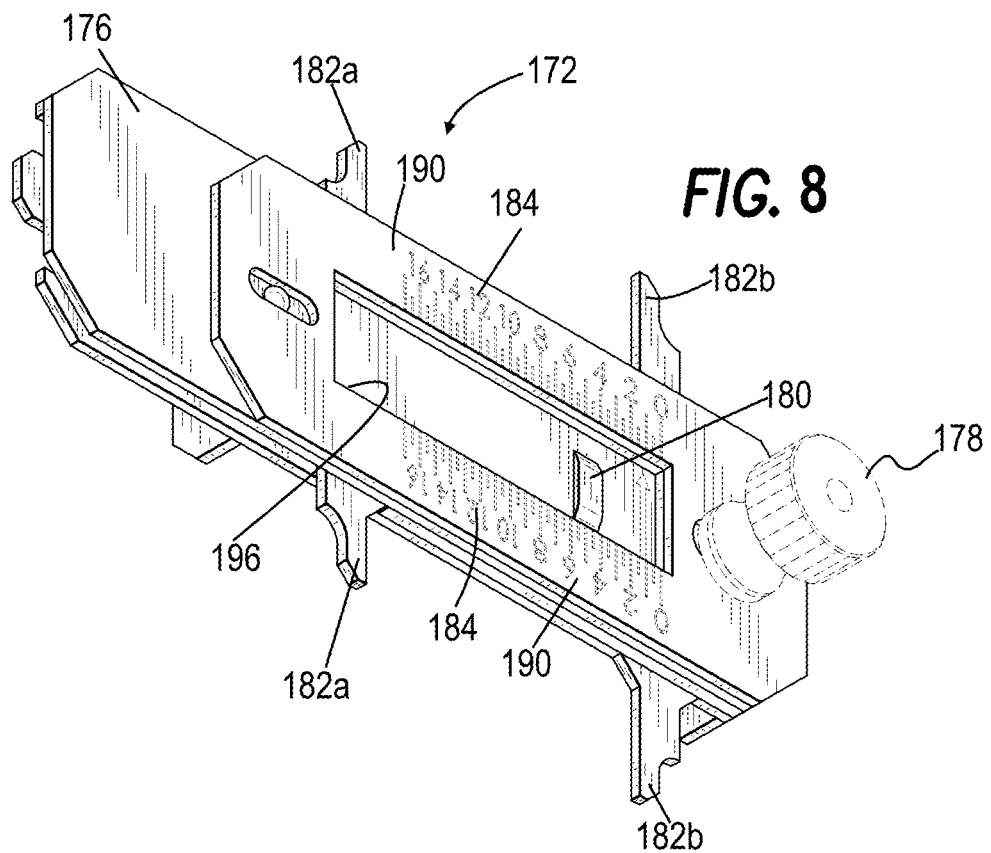
FIG. 8 is a bottom front perspective view of the length gauge of FIG. 7.
Figure 9:
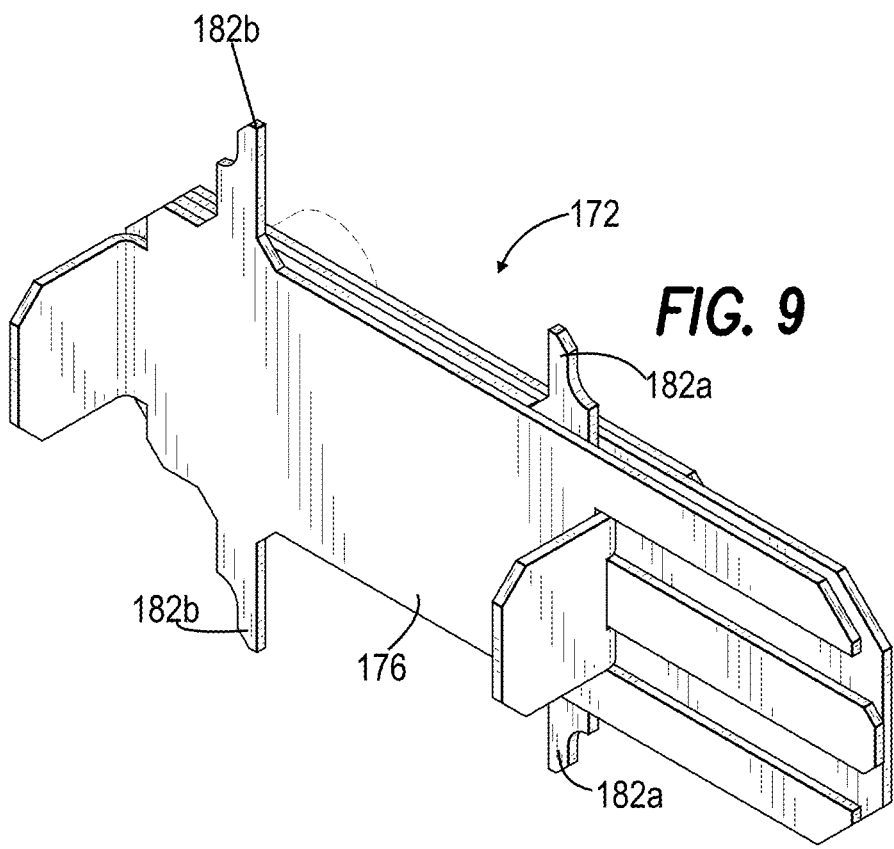
FIG. 9 is a rear top left perspective view of the length gauge of FIG. 7.
Figure 10:
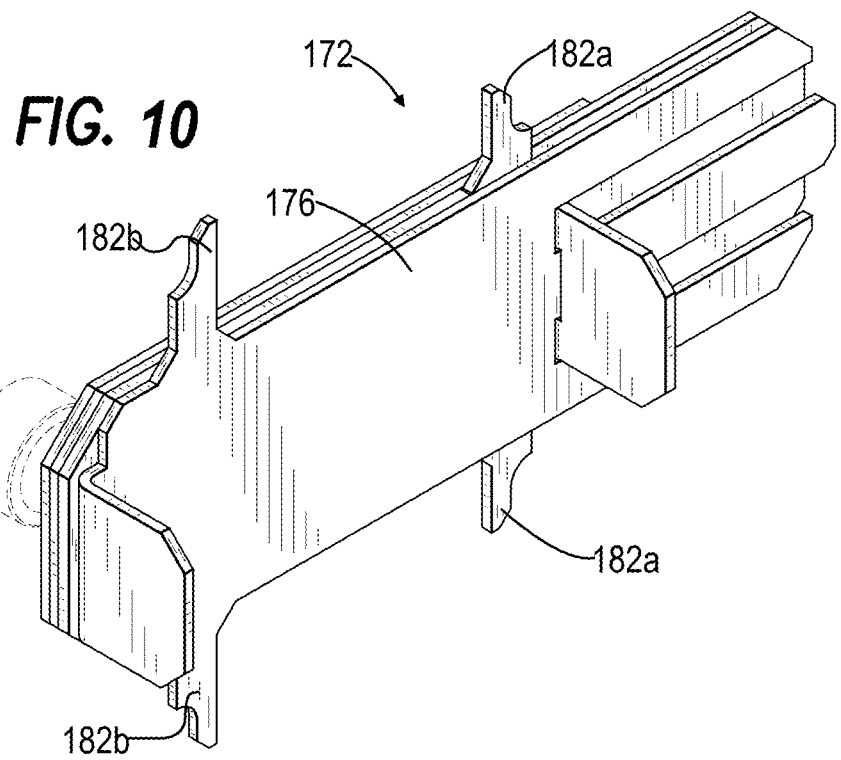
FIG. 10 is a rear top right perspective view of the length gauge of FIG. 7.
Figure 11:
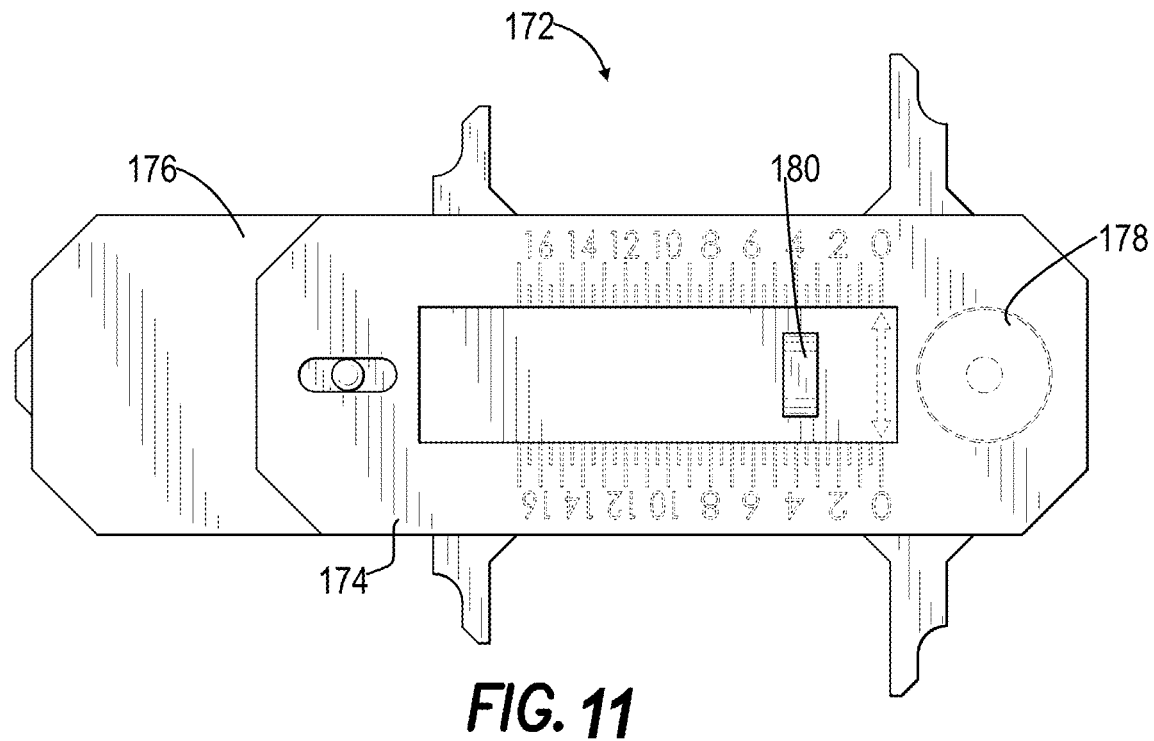
FIG. 11 is a front view of the length gauge of FIG. 7.
Figure 12:
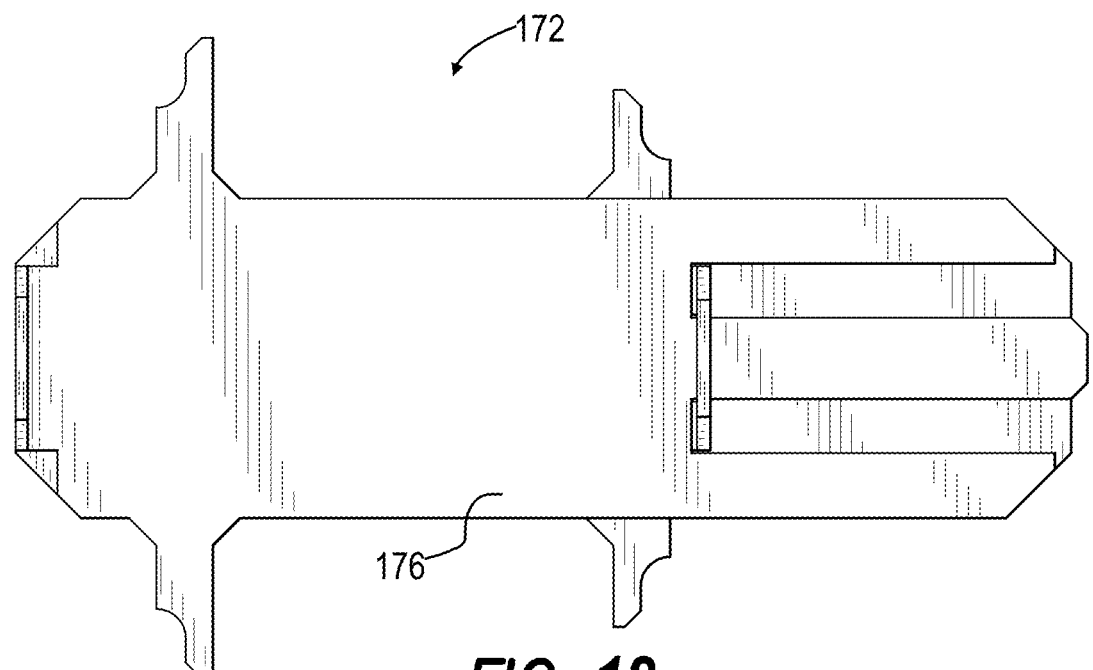
FIG. 12 is a rear view of the length gauge of FIG. 7.
Figure 13:
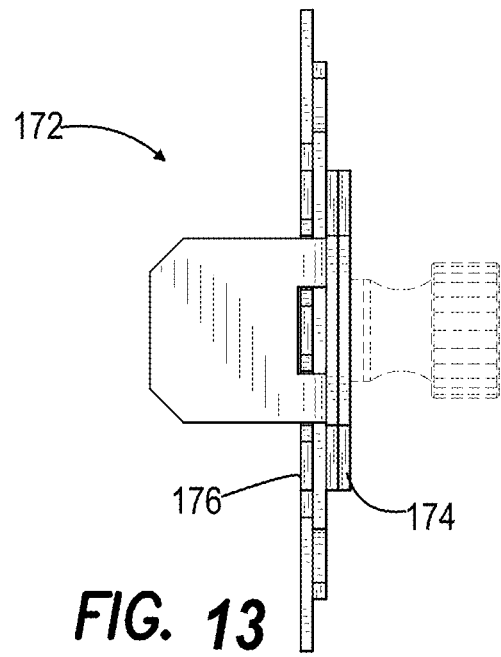
FIG. 13 is a left side elevated view of the length gauge of FIG. 7.
Figure 14:
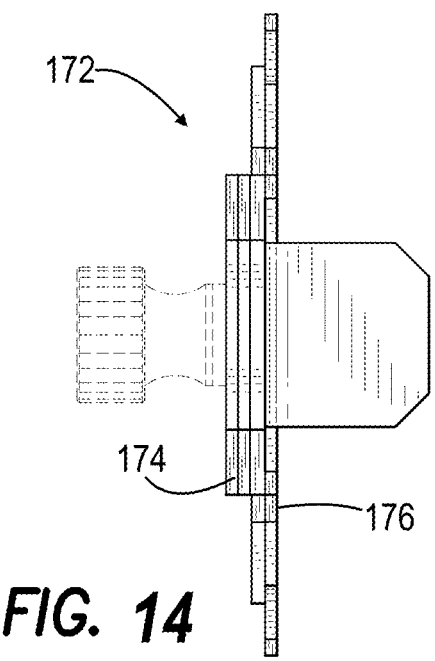
FIG. 14 is a right side elevated view of the length gauge of FIG. 7.
Figure 15:
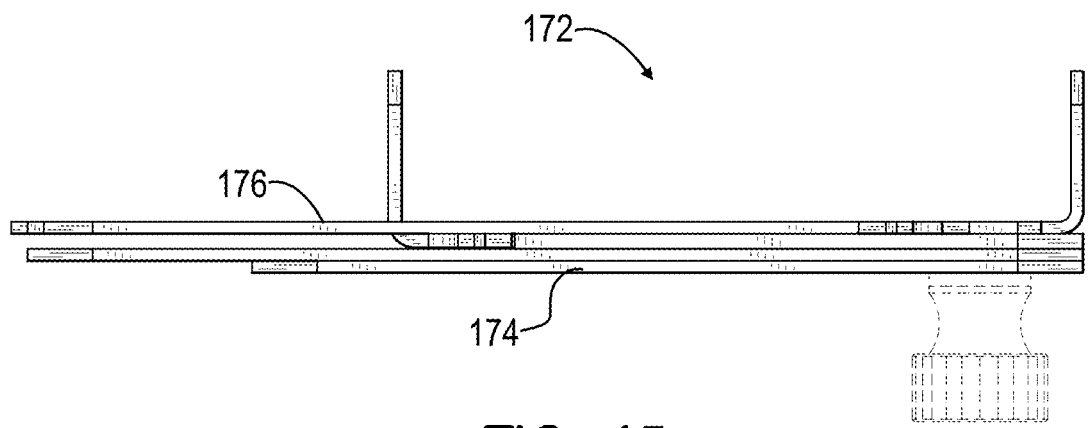
FIG. 15 is a top elevated view of the length gauge of FIG. 7.
Figure 16:
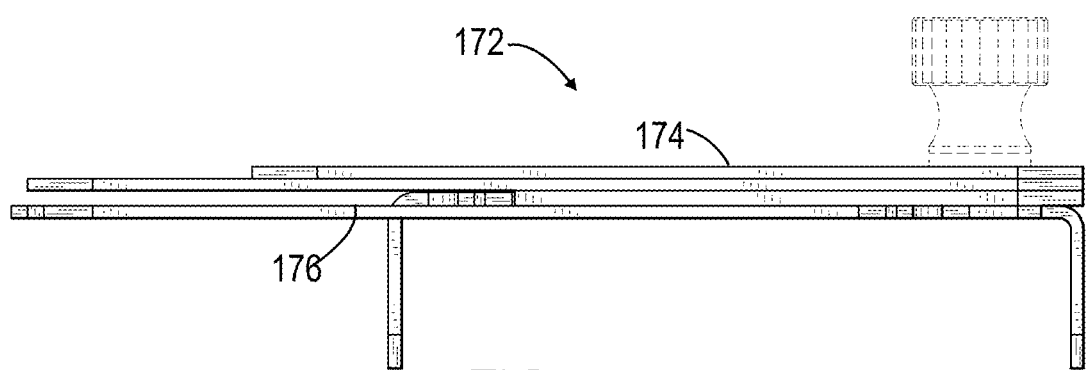
FIG. 16 is a bottom elevated view of the length gauge of FIG. 7.
Figure 17:
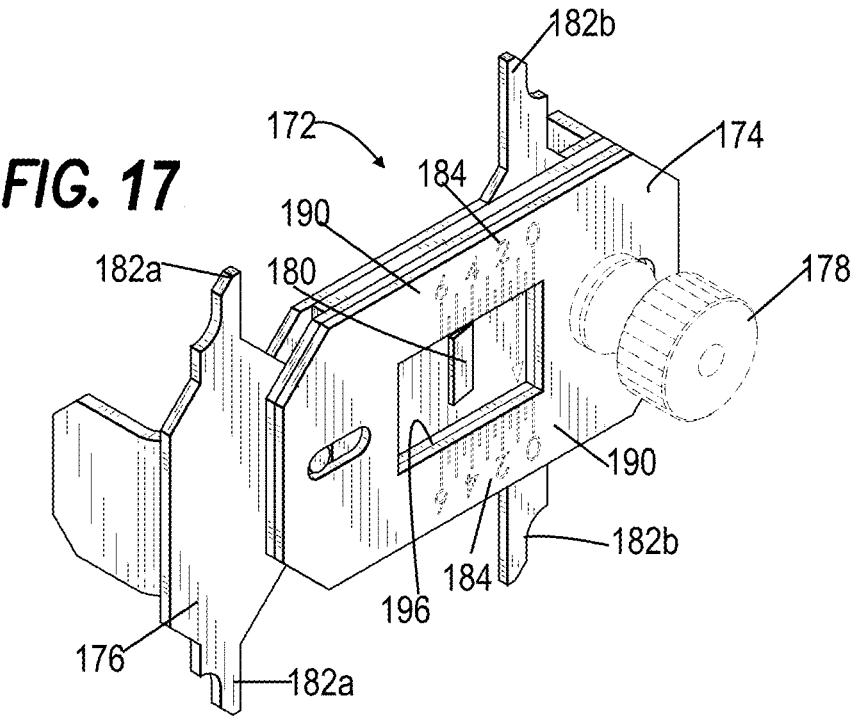
FIG. 17 is a top front perspective view of a length gauge that may be used to measure the length of a strut assembly, according to an embodiment.
Figure 18:
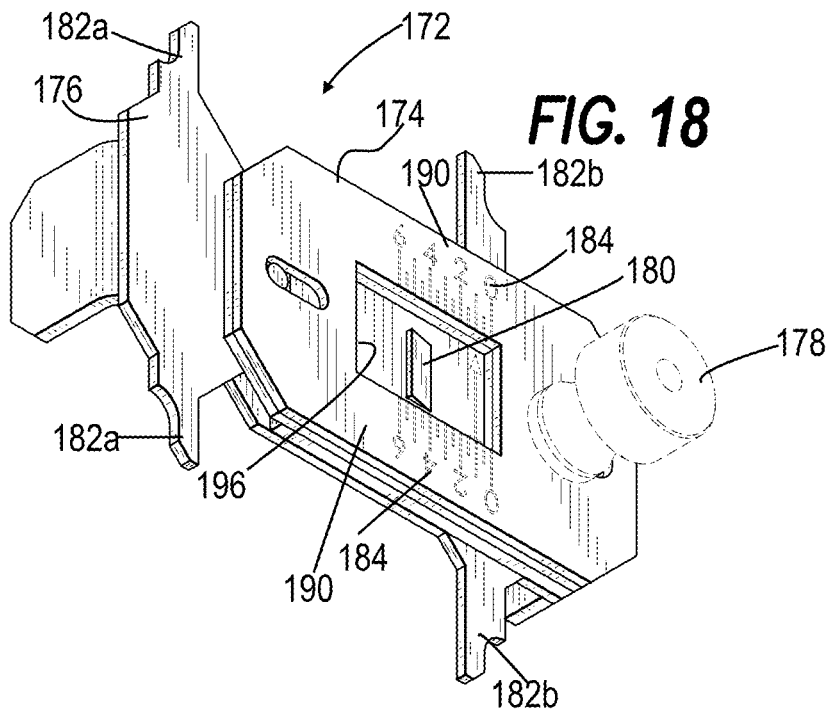
FIG. 18 is a bottom front perspective view of the length gauge of FIG. 17.
Figure 19:
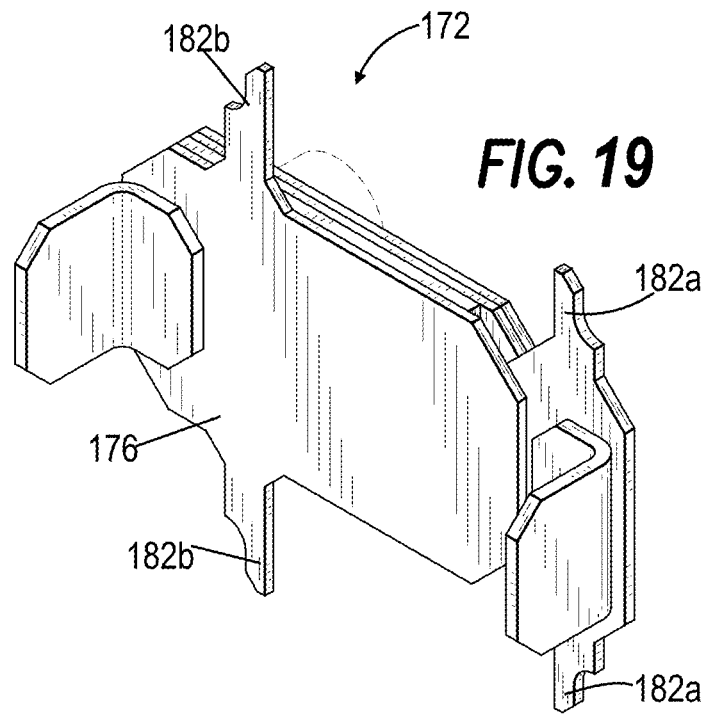
FIG. 19 is a rear top left perspective view of the length gauge of FIG. 17.
Figure 20:
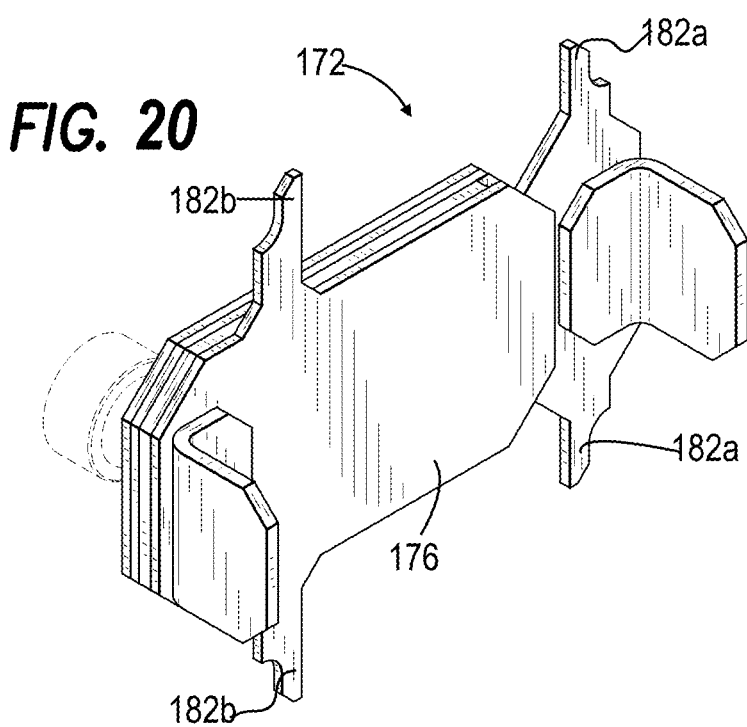
FIG. 20 is a rear top right perspective view of the length gauge of FIG. 17.
Figure 21:
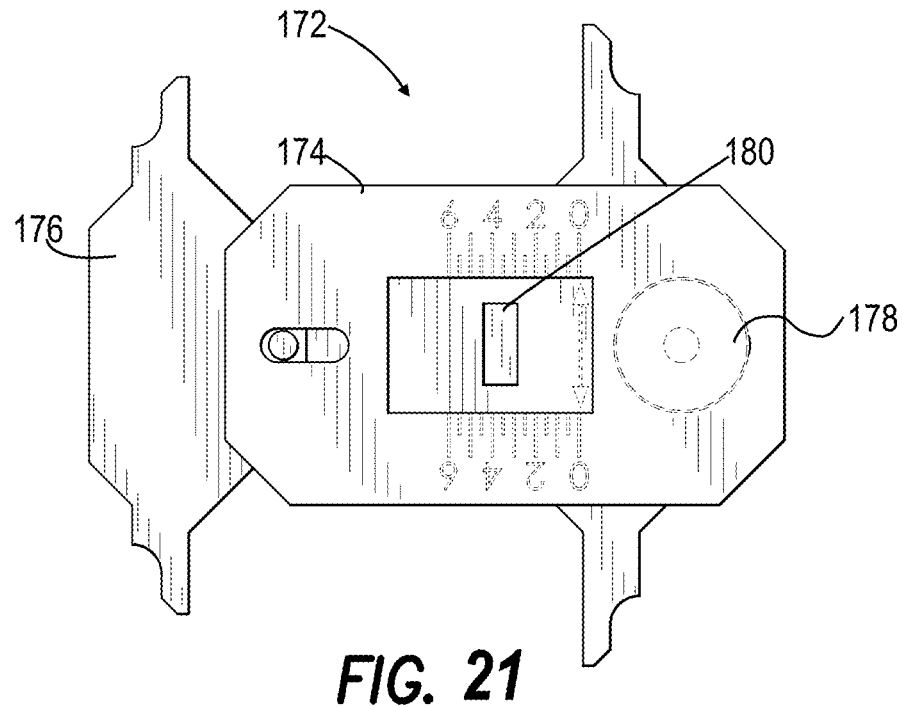
FIG. 21 is a front view of the length gauge of FIG. 17.
Figure 22:
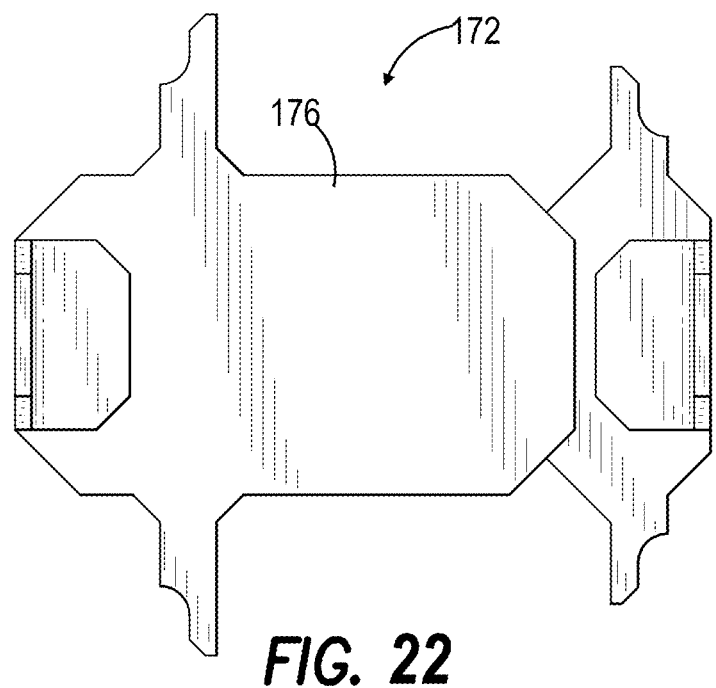
FIG. 22 is a rear view of the length gauge of FIG. 17.
Figure 23:
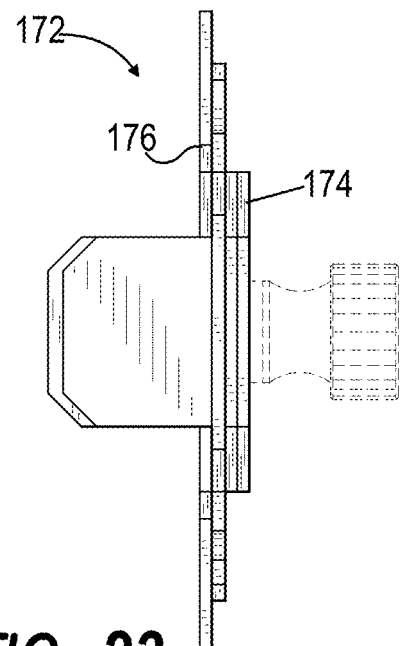
FIG. 23 is a left side elevated view of the length gauge of FIG. 17.
Figure 24:
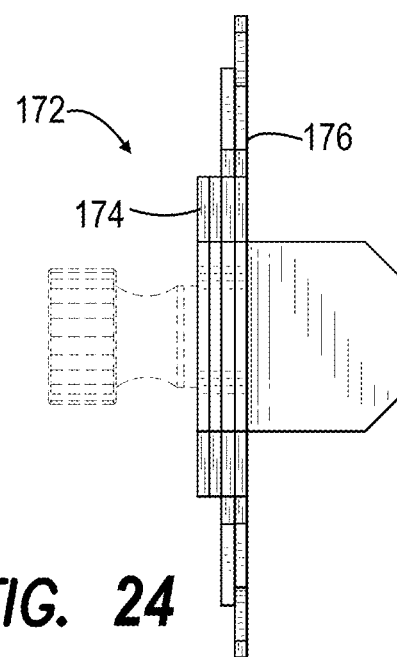
FIG. 24 is a right side elevated view of the length gauge of FIG. 17.
Figure 25:
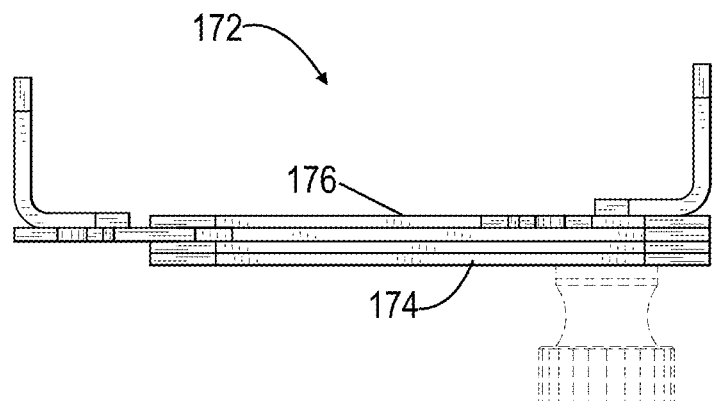
FIG. 25 is a top elevated view of the length gauge of FIG. 17.
Figure 26:
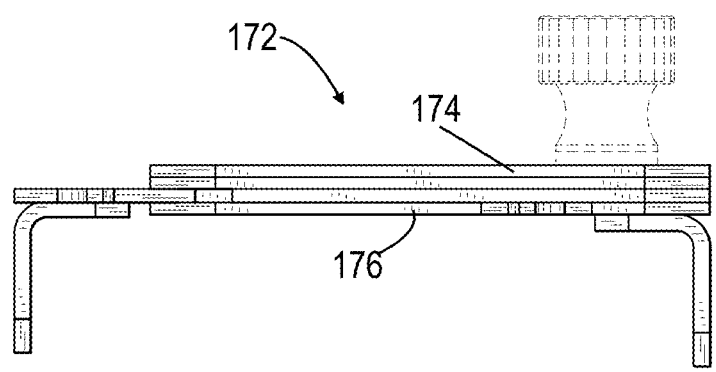
FIG. 26 is a bottom elevated view of the length gauge of FIG. 17.

As will be discussed further below, the appliance 100 may be adjusted so that the lower tray 104 is offset from the upper tray 102 to maintain the user's lower jaw in a protruded (i.e., forwardly urged) position, in accordance with treatment protocol for sleep apnea, as shown schematically in FIG. 1B and FIG. 6C. For example, the lower tray 104 may be urged forward (i.e., offset) a distance of up to 10 mm (e.g., in up to about 0.5 mm increments), for example, from about 2 mm to about 5 mm, for example, about 3.5 mm. Urging of the lower jaw in a forward direction helps to advance the patient's mandible and move the tongue forward, thereby increasing the space in the posterior part of the patient's throat and the oropharynx to increase the flow of air during the patient's sleep.

Figure 1B:
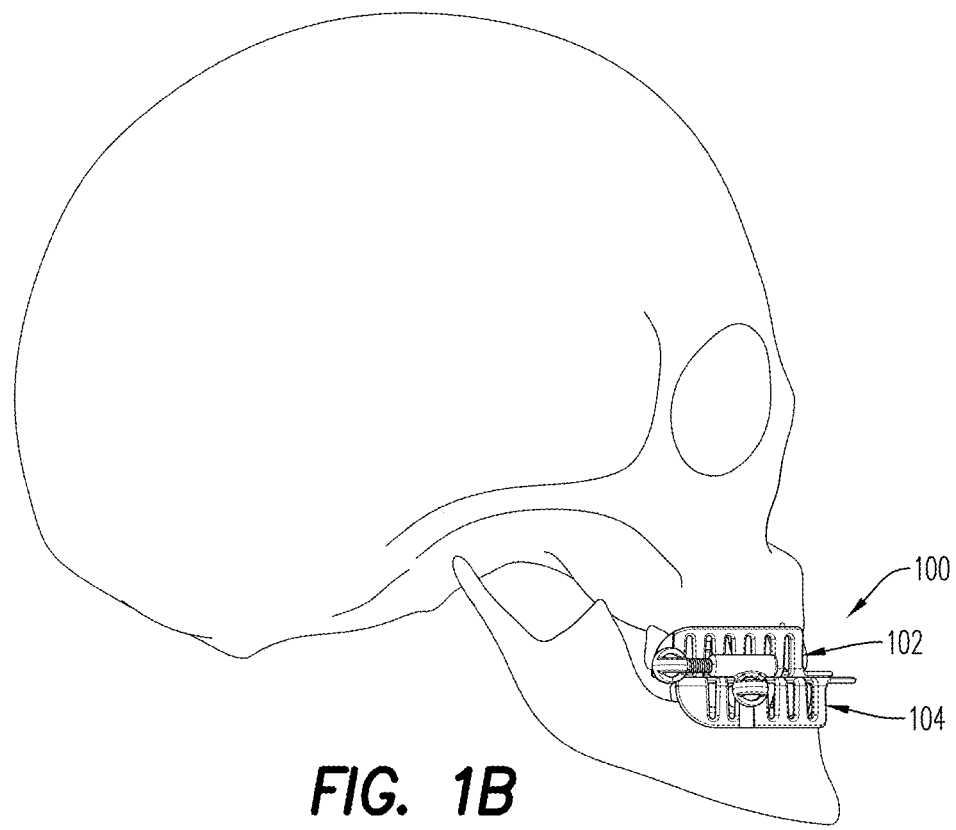
FIG. 1B is a schematic, side view of the provisional oral appliance of FIG. 1A, in use.
Figure 1C:
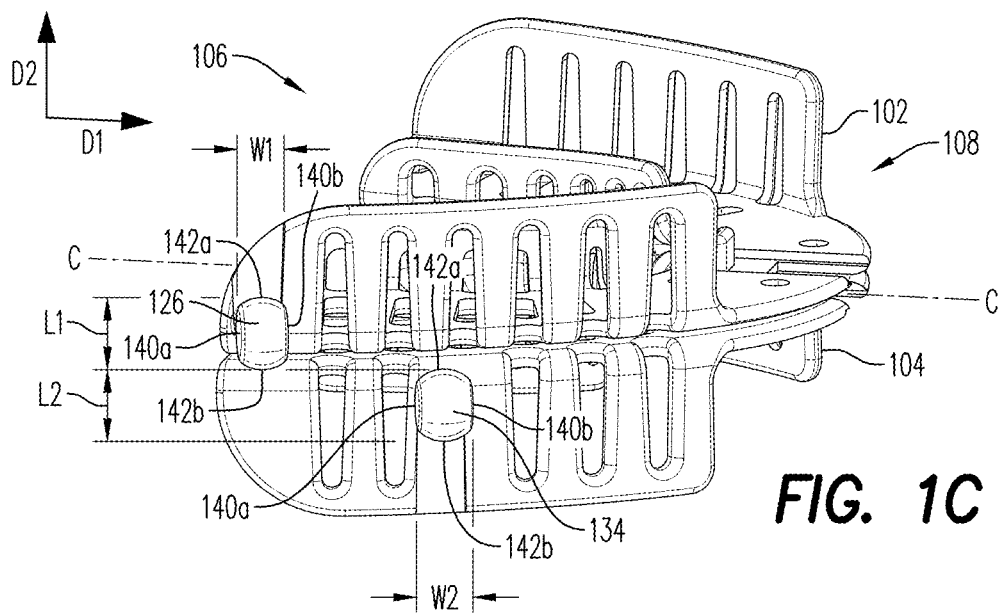
FIG. 1C is a schematic, side view of the trays of the provisional oral appliance of FIG. 1A, in isolation.

Viewing FIG. 1A, FIG. 6A, and FIG. 6B in greater detail, the appliance 100 includes a pair of struts or strut assemblies 112 pivotably (e.g., rotatably) connected to the upper tray 102 and lower tray 104 at respective upper (i.e., posterior) and lower (i.e., anterior) joints or hinges 114, 116, for example, ball-type joints (e.g., ball/socket joints, not all of which are labeled in FIG. 1A and FIGS. 6A-6B) positioned along opposed lateral sides of the appliance 100. When the upper and lower trays 102, 104 are in a closed position, the strut assemblies 112 extend generally along and across (but not exactly parallel to) a centroidal axis C (e.g., extending generally in a direction D1) between the upper and lower trays 102, 104 (FIG. 1C).

Each strut assembly 112 includes a male portion (e.g., piece/part) 118 and a female portion (e.g., piece/part) 120 configured to engage one another and the upper and lower trays 102, 104. Specifically, the male portion 118 of each strut assembly 112 includes a rod 122. In the embodiment illustrated in FIG. 1A, the male portion 118 also includes a generally cuplike (i.e., spherical or concave) socket 124 (i.e., posterior socket) for mating with or receiving a corresponding ball/projection 126 (i.e., posterior projection) extending outwardly from a buccal surface of the upper tray 102 proximate to the posterior end 106 of the appliance 100. When engaged with one another, each posterior socket 124 and corresponding projection 126 collectively form the upper joints 114 (i.e., posterior joints). The female portion 120 of each strut assembly 112 includes a tube-like cylinder 128 (with an open interior space/bore 130) and, in the embodiment illustrated in FIG. 1A, a generally cuplike (i.e., spherical or concave) socket 132 (i.e., anterior socket) for mating with a corresponding ball/projection 134 (i.e., anterior projection) projecting (i.e., extending outwardly) from a buccal surface of the lower tray 104 (e.g., positioned substantially midway between the posterior and anterior ends 106, 108 of the lower tray 104 along a direction D1). When engaged with one another, each socket 132 and corresponding projection 134 collectively form the lower joints 116 (i.e., anterior joints).

The rod 122 and cylinder 128 of each strut assembly 112 of FIG. 1A and FIGS. 6A-6B engage one another via respective mating threads 136, 138. The respective mating threads 136, 138 may be formed on the exterior surface of the rod 122 (FIGS. 6I-6K) and the interior surface of the cylinder 128 (FIGS. 6D-6E and FIG. 6H), such that the rod 122 is at least partially threaded into and at least partially received within the interior space (i.e., threaded bore) 130 of the cylinder 128. For example, in one embodiment, each rod 122 includes a male screw thread 136 (e.g., 2.5-0.45 mm, alternatively, 3.0-0.5 mm) that mates with a corresponding female screw thread 138 (e.g., 2.5-0.45 mm, alternatively, 3.0-0.5 mm) in the respective cylinder 128 to form the strut assemblies 112.

For each strut assembly 112, the rod 122 may be screwed into the cylinder 128 and adjusted to the appropriate length after the upper tray 102 and the lower tray 104 are set to the desired bottom jaw protrusive position (see, for example, FIG. 6C) by rotating the rod 122 full 360-degree revolution increments, indicative of a forward protrusive movement of the strut assembly 112 (and therefore the lower tray 104). Once set, this establishes a final, repeatable positioning of the lower jaw relative to the upper jaw for the appliance. Thus, while joints 114, 116 allow for some degree of lateral as well vertical movement of the lower tray 104 relative to the upper tray 102, for example, to accommodate grinding, clenching, yawning or swallowing, the lower jaw is prevented from moving in a retrusive (i.e., backward) direction from the predetermined treatment position.

As best seen in FIG. 1C, which schematically depicts trays 102, 104 in isolation, the projections 126, 134 of the trays 102, 104 are somewhat spherical in shape with a pair of opposed planar surfaces 140a, 140b respectively facing the posterior end 106 and anterior end 108 of the appliance 100. The projections 126, 134 each generally resemble a truncated prolate spheroid (e.g., a sideways barrel shape or flattened ball shape), such that when viewed in side elevation (as substantially shown in FIG. 1C), the projections 126, 134 have an obround shape (i.e., a somewhat elongate shape with substantially straight, planar sides 140a, 140b and curved upper and lower surface portions 142a, 142b). It will be understood that the upper and lower surface portions comprise parts of a continuous curved surface extending between the sides/planar surfaces 140a, 140b. Thus, the terms "upper" and "lower" are used merely for convenience and ease of explanation, and are not intended to be limiting in any manner. Projection 126 has a first/minor dimension (e.g., a width W1) extending in a direction D1 between opposed planar surfaces 140a, 140b and a second/major dimension (e.g., a length L1) extending in a direction D2 between curved upper and lower surface portions 142a, 142b of the projection 126. Similarly, projection 134 has a first/minor dimension (e.g., a width W2) extending in a direction D1 between opposed planar surfaces 140a, 140b and a second/major dimension (e.g., a length L2) extending in a direction D2 between curved upper and lower surface portions 142a, 142b of the projection 134. In some embodiments, the respective dimensions L1, L2 and W1, W2 of the projections 126, 134 may be the same. In other embodiments, the respective dimensions L1, L2 and W1, W2 of the projections 126, 134 may differ from one another. It will be appreciated that the other side of the trays 102, 104 (and therefore projections 126, 134 on the other side of the trays 102, 104) may generally be configured as a mirror image of the illustrated side of the trays 102, 104.

Figure 1D:
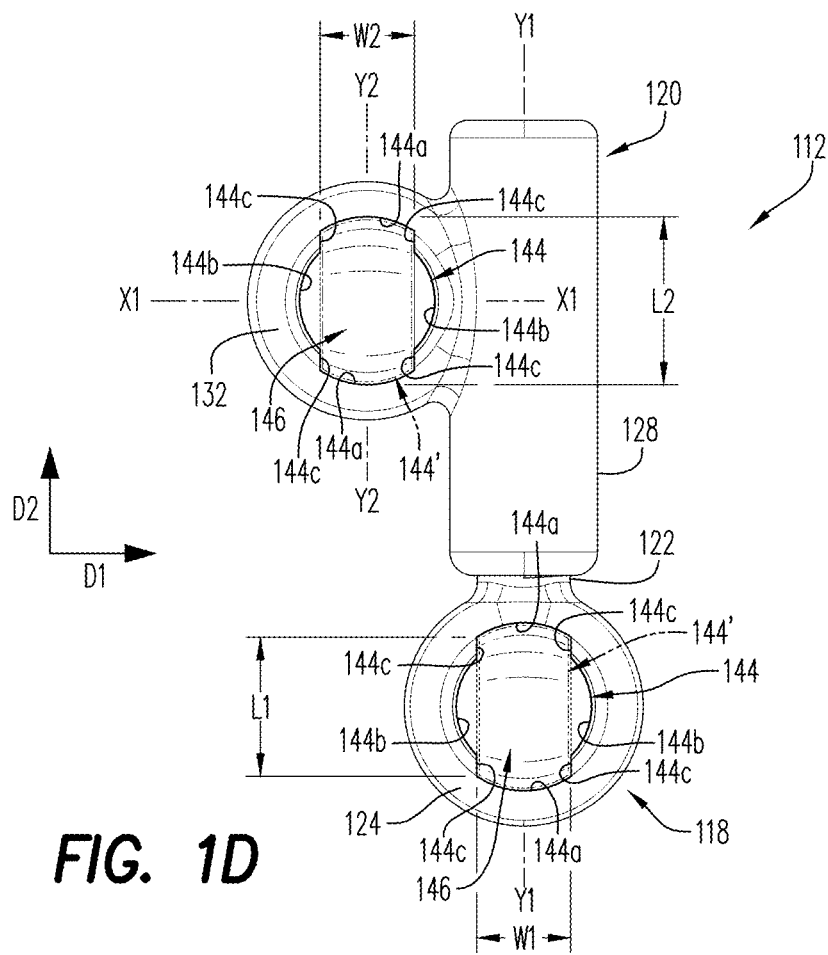
FIG. 1D is a schematic, side view of one strut assembly of the provisional oral appliance of FIG. 1A, in isolation.

FIG. 1D schematically illustrates one of the strut assemblies 112 in isolation and oriented in a vertical configuration, as compared with its generally horizontal configuration during use. It will be appreciated that the other strut assembly (not shown) may generally be configured as a mirror image of the illustrated strut assembly.

As shown in FIG. 1D, the sockets 124, 132 of the male portion 118 and the female portion 120 each include an opening 144 and a cuplike (i.e., spherical or concave) interior space 146. The opening 144 (e.g., overall/major opening) is defined generally (i.e., along a peripheral edge) by a first pair of opposed curved edge portions 144a extending generally in a direction D1, a second pair of opposed curved edge portions 144b extending generally in a direction D2, and plurality of substantially straight/linear edge portions 144c extending generally in a direction D2 between and connecting the adjacent curved edge portions 144a, 144b.

The first pair of opposed curved edge portions 144a and the plurality of straight/linear edge portions 144c (with imaginary/theoretical extensions drawn between the linear edge portions 144c in a direction D2) can be viewed as defining a generally obround opening 144' (e.g., a minor/keyed opening) (i.e., a generally rectangular shaped opening with curved ends along the shorter sides of the rectangle), as delineated schematically with dashed lines in FIG. 1D. The keyed or minor opening 144' of each socket 124, 132 may be viewed as a subset or portion of the major opening 144.

The opening 144' of the posterior socket 124 has a first/minor dimension (e.g., a width W1) extending in a direction D1 between opposed linear edge portions 144c and a second/major dimension (e.g., a length L1) extending in a direction D2 between opposed curved edge portions 144a of the socket 124. Likewise, the opening 144' of anterior socket 132 has a first/minor dimension (e.g., a width W2) extending in a direction D1 between opposed linear edge portions 144c and a second/major dimension (e.g., a length L2) extending in a direction D2 between opposed curved edge portions 144a of the anterior socket 132. In some embodiments, the respective dimensions L1, L2 and W1, W2 of the sockets 124, 132 may be the same. In other embodiments, the respective dimensions L1, L2 and W1, W2 of the sockets 124, 132 may differ from one another.

Additionally, as shown in FIG. 1D, in this example, the rod 122 and the posterior socket 124 (and cylinder 120) are arranged in a colinear relationship; that is, the center of the socket 124 and the rod 122 (and cylinder 120) each lie along a central lengthwise or longitudinal axis Y1 extending in a direction D2 (with the length L1 of opening 114' extending in the direction D2). In contrast, the central lengthwise or longitudinal axis Y2 (extending in a direction D2) of socket 132 is generally parallel to the central longitudinal axis Y1 of cylinder 120 (and rod 122 and socket 124) (with the length L2 of opening 114' of socket 132 extending in the direction D2). A transverse axis X1 extending in a direction D1 of socket 132 is generally perpendicular to the central longitudinal axis Y1 of cylinder 120 (and rod 122 and socket 124). As a result, the strut assemblies 112 have an overall somewhat L-shape defined along axes X1 and Y1. However, other possible configurations are contemplated hereby.

As will be understood from FIGS. 1C and 1D, the opening 144 of sockets 124, 132 and the respective mating projections 126, 134 are shaped and dimensioned to be "keyed" to one another. That is, projections 126, 134 can only be inserted into respective sockets 124, 132 when the projections are 126, 134 are properly aligned with (i.e., in "shape alignment" with) the keyed/minor opening 144' of the respective socket 124, 132. Specifically, in the illustrated embodiment, projection 126 can only be inserted into the posterior socket 124 when the curved portions 142a, 142b of the projection 126 and the curved portions 144a of the opening 144' are aligned with one another, and the planar portions/surfaces 140a, 140b of the projection 126 and the linear portions 144c of the opening 144' are aligned with one another. Likewise, projection 134 can only be inserted into anterior socket 132 when the curved portions 142a, 142b of the projection 134 and the curved portions 144a of the opening 144' of socket 132 are aligned with one another, and the planar portions/surfaces 140a, 140b of projection 134 and the linear portions 144c of the opening 144' of socket 132 are aligned with one another. Thus, it will be appreciated that the dimensions L1, W1 of the posterior socket 124 may be substantially the same as the dimensions L1, W1 of projection 126, and the dimensions L2, W2 of the anterior socket 132 may be substantially the same as the dimensions L2, W2 of projection 134. In some embodiments, the dimensions of the projections 126, 134 may be slightly larger than the respective dimensions of anterior and posterior sockets 132, 124 to provide a "snap" fit when connecting the strut assemblies 112 to the trays 102, 104.

To attach each strut assembly 112 to the upper tray 102, the strut assembly 112 must be oriented in a direction generally perpendicular to the plane of the tray (e.g., in an upright/vertical direction D2 relative to the tray, as shown in FIG. 1D). To do so, either the upper tray 102 or the strut assembly 112 may be rotated into a perpendicular position to achieve shape alignment of the projection 126 and the posterior socket 124. Once the projection 126 is inserted into the socket 124 to form the posterior joint 114, the strut assembly 112 may be rotated (i.e., pivoted) along the posterior joint 114 to bring the strut assembly 112 into a generally aligned/horizontal position, so that the longitudinal axes Y1, Y2 of the strut assembly 112 extend generally in a direction D1 (i.e., generally extending along the plane of the tray). In the generally horizontal position, the curved portions 142a, 142b of the projection 126 and the curved portions 144a of the opening 144' of the posterior socket 124 are no longer aligned with one another, and the planar portions 140a, 140b of the projection 126 and the linear portions 144c of the opening 144' are no longer aligned with one another, so the projection 126 can no longer be removed from the socket posterior 124. Thus, rotation of the rod 122/strut assembly 112 locks the projection 126 into the interior space 146 of the posterior socket 124, and therefore, provides a secure connection between the strut assembly 112 to the upper tray 102 without concern for inadvertent detachment. Additionally, as stated above, the projection 126 may be dimensioned to be slightly larger than the opening 144' so that the projection 126 "snaps" into the posterior socket 124. This provides additional security in preventing the parts from becoming detached inadvertently.

Likewise, to attach each strut assembly 112 to the lower tray 104 (after adjusting the length of the strut assembly as discussed above), the strut assembly 112 must be oriented in a direction generally perpendicular to the plane of the tray (e.g., in an upright/vertical direction D2 relative to the tray, as shown in FIG. 1D). In this case, for example, the lower tray 104 may be rotated vertically (i.e., at a 90-degree angle to socket 132). Once the projection 134 and anterior socket 132 are mated with one another to form the anterior joint 116, the lower tray 104 may then be reverted back to its horizontal position, so that the strut assembly 112 and lower tray 104 are secured to one other, as described above with respect to the posterior joint 114. As above, projection 134 may be dimensioned to snap into the anterior socket 132 if desired. If further adjustments are necessary, the above process may be reversed to detach the anterior socket 132 of the strut assembly 112 from the anterior projection 134 of the tray 104, and so on.

As discussed above, once the strut assemblies 112 have been set to the desired length and attached to the trays 102, 104, the lower jaw is in a fixed position relative to the upper jaw. Thus, although joints 114, 116 allow for some lateral and vertical movement of the lower tray 104 relative to the upper tray 102 to accommodate typical jaw movements, the lower jaw is prevented from moving in a retrusive (i.e., backward) direction away from the necessary treatment position.

The various parts of the appliance may generally be made from materials that are suitable for use in an oral cavity, including, for example, stainless steel or any other surgical grade metal alloy, or any biocompatible, non-metallic material (including BPA free material), such as polymeric materials (i.e., polymers). For example, the trays may be made of a polymeric material (i.e., polymer) having a shore hardness of from about 60 to about 70, such as polypropylene. The parts of the strut assemblies 112 may likewise be made of a polymeric material, for example, polycarbonate or polyester.

The various parts of the appliance may likewise be made in any suitable manner, for example, using injection molding, 3D printing, or any other suitable technique. In one aspect, the various parts of each strut assembly may be made from a moldable material, such as a polymeric material (e.g., a polymer), so that parts of the strut assemblies may be integrally formed with one another. For example, the rod 122 and socket 124 may be formed from as a unitary, one-piece structure 118, for example, molded from a polymeric material with the rod 122 and socket 124 integrally formed with and joined to one another. Likewise, cylinder 128 and anterior socket 132 may be formed from as a unitary, one-piece structure 120, for example, molded from a polymeric material with the cylinder 128 and anterior socket 132 integrally formed with and joined to one another. Thus, each strut assembly 112 may be a two-piece structure formed entirely from moldable polymeric materials with the respective parts of the male and female portions 118, 120 integrally formed with and joined to one another. This provides a significant advantage over other appliance designs, in which small screws, brackets, or other parts are used to connect the components of the appliance. Such small pieces may tend to loosen and/or may be inadvertently lost or swallowed if not handled with extreme care. Thus, the simplicity of the two-piece structure 118, 120 described herein not only makes the device significantly less complicated, but also safer to work with and wear.

It will be appreciated that although one exemplary configuration of the strut assemblies 112 and trays 102, 104 is illustrated herein, other possibilities are contemplated hereby.

For example, it is contemplated that the relative positions of the projections may be inverted relative to the upper and lower trays 102, 104, such that projection 126 extends from the posterior end 106 of the lower tray 104, and projection 134 extends from the upper tray 104 (e.g., positioned substantially midway between the posterior and anterior ends 106, 108 of the upper tray 102). Likewise, it is contemplated that the male portion 118 of the strut 112 and/or the female portion 120 of the strut 112 may include either or both of projections 126, 134, and the upper tray and/or lower tray 102, 104 may include the respective sockets 124, 132. Other possible configurations are contemplated.

FIGS. 6D-6K illustrate alternate embodiments of the female portion 120 and the male portion 118 of the strut 112, whereby the female portion 120 (shown, for example, in FIGS. 6D-6H) includes a ball/projection 126 (i.e., anterior projection) projecting (i.e., extending outwardly) from the cylinder 128 and the male portion 118 (shown, for example, in FIGS. 6I-6K) includes a ball/projection 126 (i.e., anterior projection) projecting (i.e., extending outwardly) from the rod 122. When each posterior socket 124 and corresponding projection 126 are engaged with one another, the socket and projection combination collectively form the upper joints 114 (i.e., posterior joints) as seen in FIGS. 6A-6B.

The female portion 120 of each strut assembly 112 includes a tube-like cylinder 128 and an open interior space/bore 130 extending along the length of the cylinder 128 from a first end of the cylinder 128. A ball/projection 126 is formed at a second end of the cylinder 128 spaced apart from the first end of the cylinder 128 and is receivable in a generally cuplike (i.e., spherical or concave) posterior socket 124 (i.e., the posterior socket) of the strut assembly 112. The male portion 118 includes a rod 122 and a ball/projection 134 (i.e., anterior projection) projecting (i.e., extending outwardly) from the rod 122. According to an aspect, the projection 134 is configured to engage with the anterior socket 132 of the strut assembly 112, such that the corresponding anterior socket 132 and corresponding projection 134 collectively form the lower joints 116 (i.e., anterior joints). The posterior socket 124 extends from the buccal surface of the upper tray 102, while the anterior socket 132 extends from the buccal surface of the lower tray 104.

As described hereinabove with respect to FIGS. 1A and 1D, the rod 122 and cylinder 128 of each strut assembly 112 engage one another via respective mating threads 136, 138 formed on the exterior surface of the rod 122 and formed on the interior surface of the cylinder 128. In this configuration, the rod 122 can be at least partially threaded into and at least partially received within the interior space (i.e., threaded bore) 130 of the cylinder 128. The rod 122 may be screwed into the cylinder 128 and adjusted to the appropriate length after the upper tray 102 and the lower tray 104 are set to the desired bottom jaw protrusive position by rotating the rod 122 in various degree increments, such as 360-degree revolution increments, which is indicative of a forward protrusive movement of the strut assembly 112 (and therefore the lower tray 104) (FIG. 6C). Once set, this establishes a final, repeatable positioning of the lower jaw relative to the upper jaw for the appliance 100. Thus, while joints 114, 116 allow for some degree of lateral as well vertical movement of the lower tray 104 relative to the upper tray 102, for example, to accommodate grinding, clenching, yawning or swallowing, the lower jaw is prevented from moving in a retrusive (i.e., backward) direction from the predetermined treatment position.

The projections 126, 134 may be configured in various shapes. As illustrated in FIGS. 6D-6F, 6H-6I and 6K, the projections 126, 134 may be spherical in shape with a pair of opposed planar surfaces 141a, 141b (i.e., oblate) respectively facing the posterior end 106 and anterior end 108 of the appliance 100. In this configuration and as described hereinabove with respect to FIGS. 1A, 1C and 1D, the projections 126, 134 each generally resemble a truncated prolate spheroid, such that when viewed from the side (as substantially shown in FIGS. 6F and 6K), the projections 126, 134 have an obround shape. According to an aspect, the upper and lower surface portions comprise parts of a continuous curved surface extending between the sides/planar surfaces 141a, 141b.

Each of the posterior and anterior sockets 124, 132 may include an opening and a cuplike (i.e., spherical or concave) interior space (not shown in FIGS. 6A-6K, but generally illustrated in FIGS. 1A and 1D). The cuplike interior space defines a generally obround opening, having a generally rectangular shaped opening with curved ends along the shorter sides of the rectangle, as delineated schematically with dashed lines in FIG. 1D.

It is contemplated that the opening of the posterior and anterior sockets 124, 132 and the respective mating projections 126, 134 may be shaped and dimensioned to be "keyed" to one another. That is, the projections 126, 134 can only be inserted into respective sockets 124, 132 when the projections 126, 134 are properly aligned with (i.e., in "shape alignment" with) the keyed opening of the respective socket 124, 132. According to an aspect, the projection 126 may be dimensioned to be slightly larger than the opening so that the projection 126 essentially "snaps" and locks into the posterior socket 124. Similarly, the projection 134 may also be configured to "snap" and lock into the anterior socket 132. This provides additional security in preventing the parts from becoming detached inadvertently.

It is also contemplated that one or more of joints 114, 116 may include a non-keyed configuration. For example, one or more of joints 114, 116 may include a generally cuplike (i.e., spherical or concave) socket that mates with a corresponding spherical or ball-shaped projection (or "ball") projecting (i.e., extending outwardly) from the respective tray. The ball and the opening of the socket may be similarly shaped and dimensioned so that the ball and socket may simply be snapped together (and unsnapped as needed) to adjust the position of the lower tray, rather than having a keyed configuration as described above.

It is further contemplated that one more of joints 114, 116 may include a projection that is permanently mated with its corresponding socket.

It is also contemplated that the strut assemblies may be configured so that the rod is capable of moving freely within the cylinder in a forward direction when the lower jaw moves forward relative to the upper jaw, so that the lower jaw can articulate more freely while being prevented from moving in a retrusive (i.e., backward) direction from the necessary treatment position.

It is further contemplated that one or both strut assemblies may include one or more features for assisting with adjusting the strut assemblies to the proper length, as needed to achieve the desired protrusive measurement. It will be noted that, although the cylinder is not precisely parallel to the centroidal axis of the upper and lower trays 102, 104 (FIG. 1C), the markings may closely correlate to the actual protrusive distance, for example, such that using the markings results a protrusive distance that is within about 2% of the desired protrusive distance.

For example, in the embodiment illustrated in FIG. 1A, the cylinder 128 may include a length/distance indicator (e.g., a ruler), for example, e.g., markings or other indicia (not shown) spaced apart from one another at particular intervals. In such an embodiment, it will be appreciated that the strut assemblies 112 may be formed from a transparent or translucent material so that the position of the end of the screw 122 can be seen through the cylinder for determining the protrusive distance.

Figure 1E:
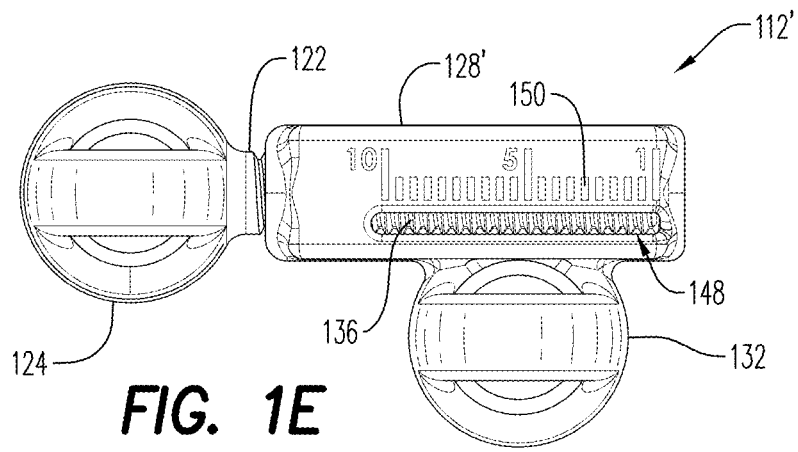
FIG. 1E is a schematic, side view of an exemplary strut assembly of the provisional oral appliance of FIG. 1A, in isolation, including a viewing window.

Alternatively or additionally, in an alternate embodiment schematically illustrated in FIG. 1E, the cylinder 128' of the strut assembly 112' may include a window (e.g., a transparent area) 148 or other feature that allows for viewing the threads 136 on the rod 122. The threads 136 on the rod 122 may be marked with length indication markings 150 to denote certain lengths, the lateral distance between the upper tray 102 and the lower tray 104 (e.g., 0.5 mm, 1 mm, etc.), or the like, as described above. While the length indication markings 150 in this example are illustrated as being spaced apart from each other at a distance of 1 mm, the markings 150 may be spaced apart from each other at other increments of about 0.89 mm, or any other suitable distance that allows each full revolution of the rod within the cylinder to adjust the lateral distance between the upper and lower trays 102, 104 in increments of 1 mm. As would be understood by one of ordinary skill in the art, the length indication markings 150 may be numerically marked to correspond with the relative lateral positioning of the upper tray 102 relative to the lower tray 104, or vice versa. If desired, at least some of the length indication markings 150 may be color-coded. For example, each major length marking (e.g., 5 mm) may be designated a different color than the minor length markings (e.g., 1 mm, 2 mm, 3 mm, 4 mm, 6 mm, 7 mm, and the like). The window 148 may further be provided with a magnifying function (not shown) (e.g., for enlarging the appearance of the threads/markings when viewed through the window), for example, by forming the window using a convex material.

Alternatively or additionally, the strut assemblies may include a length adjustment indicator to assist with adjusting the strut assemblies. For example, the strut assemblies may include an audible indicator (not shown) to improve accuracy and precision of the desired/appropriate strut assembly length, as well as the desired bottom jaw protrusive position. For example, the audible indicator may provide a distinct sound (i.e., click, tone, beep, artificial voice counter) when the rod has been rotated 360 degrees (i.e., a full revolution) in the cylinder. This helps to demonstrate, with or without a length indicator, that the strut assembly length has been adjusted, such as being reduced by or increased up to about 0.5 mm.

Alternatively or additionally, a tactile indicator may allow a user to tactilely determine (i.e., feel) whether the strut assemblies have been adjusted, without a length indicator. For example, the rod may include a flattened surface or indentation that extends along the length of the rod. The flattened surface may be formed into at least some of the male threads of the rod, and a spring may extend circumferentially around the male threads of the rod. When the rod is rotated within the cylinder, the flattened surface engages with the spring at each revolution, which provides tactile feedback to the user.

In an alternate embodiment schematically illustrated in FIGS. 1F and 1G and FIGS. 7-26, the appliance 100 (FIG. 1A) may be provided with a separate length gauge 172 for confirming/adjusting the length of each strut assembly 112 (FIG. 1A) after it has been manually adjusted to the approximate desired length.

Figure 1F:
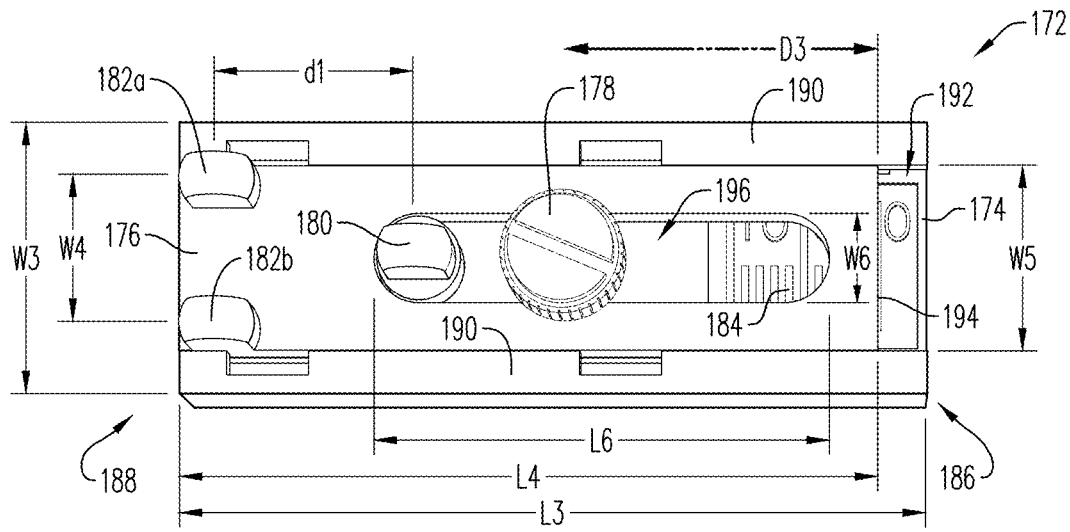
FIG. 1F is a schematic, perspective view of an exemplary length gauge that may be used to measure the length of a strut assembly, according to an embodiment.
Figure 1G:
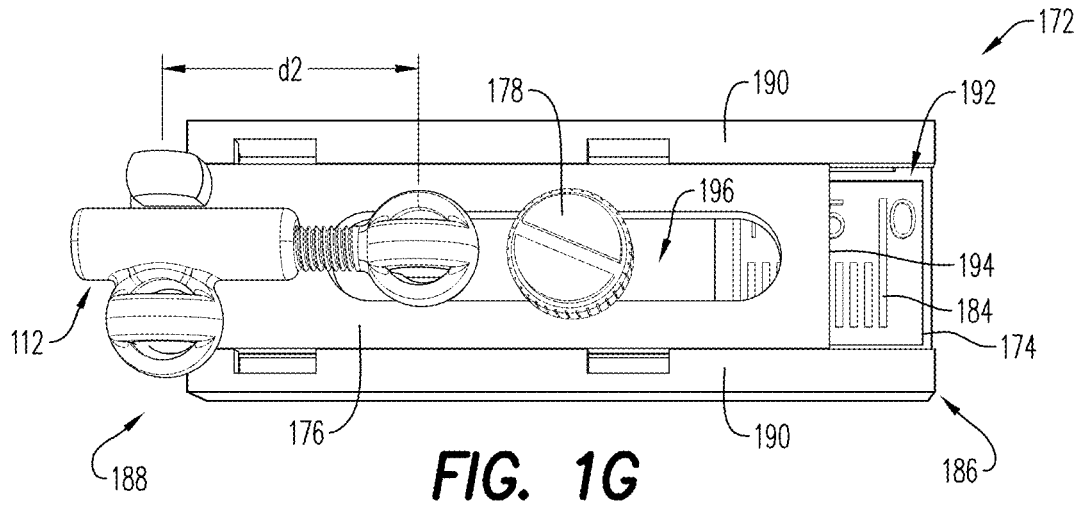
FIG. 1G schematic, perspective view of the exemplary length gauge of FIG. 1F, in use with a strut assembly.

Briefly described, the length gauge 172 may generally include a first part/base 174, a second part/slider/slider plate 176, and a fastener 178 for securing the slider 176 and base 174 in relative positions with respect to one another. The base 174 and slider 176 respectively include projections 180, 182a, 182b for temporarily mounting a strut assembly 112 (FIG. 1D) onto the gauge 172. As the slider 176 is moved relative to the base 174, the distance (e.g., d1, d2) between the projection 180 on the base and the projections 182a, 182b on the slider may be increased or decreased, as measured by length markings 184 on the base 174. With the slider 176 set at the proper distance relative to the base 174 (i.e., the desired protrusive distance) as indicated by the length markings 184, a strut assembly 112 can be temporarily attached to the projections 180, 182a, 182b on the gauge 172 to verify that the strut 112 has been set to the desired length (FIG. 1G). If adjustments are needed, the strut assembly 112 can be manually adjusted and reevaluated.

Now viewing the length gauge 172 in greater detail, the base 174 and slider 176 each generally have a first end along a first end 186 of the gauge and a second end along a second end 188 of the gauge. The base 174 and slider 176 each have a respective length L3, L4 and width W3, W4. The base 174 includes a pair of opposed sidewalls 190 that extend at least partially between the first end 186 and the second end 188 of the base 174. The sidewalls 190 define a channel 192 for receiving the slider 176. The channel 192 has a width W5 that is less than the width W3 of the base 174.

As best seen in FIG. 1G, and as mentioned above, the base 174 includes a plurality of length markings 184 positioned along the channel 192. The length markings 184 may denote a range of lengths increasing from a minimum value (e.g., zero (0)), proximate to the first end 186 of the base to a maximum value (e.g., 16 mm), moving towards the second end 188 of the base. The markings 184 may be positioned at any suitable increments, for example, at 0.05 mm or 0.1 mm increments. The lengths may generally correspond to a desired protrusive distance and to the length the strut assembly is extended beyond its minimum length.

The base 174 further includes a projection 180 (e.g., a fixed projection) extending from the base 174 within the channel 192 (projection 192 extends through opening 196, discussed below). The projection 180 is for receiving a posterior socket of a strut assembly to be evaluated (e.g., see FIG. 1A, posterior socket 124 of strut assembly 112). Accordingly, the projection 180 may be generally shaped like posterior projections 126 of tray 102, described in connection with FIG. 1A above.

The base 174 also includes a threaded bore (not shown) for receiving the threaded screw.

Returning to FIG. 1F, the slider 176 includes a first end edge 194 along the first end 186 of the slider. In the fully closed position of FIG. 1F, the first end edge 194 of the slider is aligned with the zero "0" length/distance marking. As the slider 176 is moved relative to the base 174, the first end edge 194 of the slider may be aligned with other length/distance values.

The slider 176 also includes a pair of projections 182a, 182b extending from the slider along the second end 188 of the slider. Projections 182a, 182b are for receiving an anterior socket of a strut assembly to be evaluated (e.g., see FIG. 1A, anterior socket 132 of strut assembly 112). Accordingly, projections may be generally shaped like anterior projections 134 of tray 104, described in connection with FIG. 1A above. As will be understood by those of skill in the art, since the two strut assemblies are mirror images of one another, the specific use of projection 182a or projection 182b depends on which strut assembly is being evaluated.

The slider 176 further includes an elongate aperture or opening 196 through which the base projection 180 and the screw/fastener 178 extend. The opening 196 has a length L6 and a width W6, which may generally be selected so that the slider 176 can move back and forth in a direction D3 between the minimum and maximum values of the length markings 184. As shown in FIG. 1F, base projection 180 serves as a stop point for moving the slider in a direction D3 past the minimum value (in this case zero). In this fully closed or retracted position, projections 180 and 182a, 182b are spaced apart a distance d1 that corresponds to the minimum distance between sockets 124, 132 of the strut assembly 112 (i.e., with the male portion 118 fully threaded into the female portion 120).

To use the length gauge 172 according to one exemplary method, once the proper/desired protrusive measurement has been determined (e.g., by using jig 200, discussed below), the strut assembly 112 may be manually lengthened from a closed position by turning the rod 122 a number of rotations, for example, one rotation per 0.5 mm increment. For example, where the desired protrusive measurement is 5 mm, the rod may be turned 10 times to achieve an approximate extension of 5 mm. The slider 176 on the length gauge may then likewise be moved to an extended position, so that the edge 194 of the slider is aligned with the length marking that corresponds to the desired strut assembly extension length (e.g., 5 mm in the illustrated example), and the screw 178 may be tightened. The strut assembly 112 may then be seated onto the projections 180, 182b as shown in FIG. 1G to confirm that the strut assembly has been lengthened the proper amount. It will be appreciated that since the other strut assembly is a mirror image of the illustrated strut assembly (as described above), projection 182a would be used instead of projection 182b to confirm the length of the strut assembly. If the strut assembly does not fit properly on the length gauge, the strut assembly may be lengthened or shortened as needed and reevaluated.

In another aspect, this disclosure is directed to a method of using a multipurpose jig or jig assembly to form (e.g., make and adjust) an oral appliance (such as described above). The jig assembly may be attached to the trays used in the oral appliance to assist with determining the proper protrusive measurements, and therefore, the proper length for the strut assemblies. More particularly, the jig may be used to temporarily retain a patient's upper and lower jaws in relative positions with respect to one another while the proper protrusive distance is determined and/or while any needed scans of the patient's jaw(s) are being taken. As will be discussed below, the jig attached to the trays defines an intermediate or precursor appliance assembly that advantageously facilitates both the determination of the proper protrusive measurements and fabrication of the oral appliance in a single device or structure. When the appliance is complete, the jig may be detached from the oral appliance and discarded. Accordingly, in various aspects, this disclosure is directed to a jig or jig assembly for forming an oral appliance, an intermediate or precursor appliance assembly for forming or fabricating an oral appliance, and methods of using both the jig and the precursor assembly for forming or fabricating an oral appliance. The jig assembly can also be used for other purposes, unrelated to the forming or fabrication of an oral appliance.

Figure 2A:
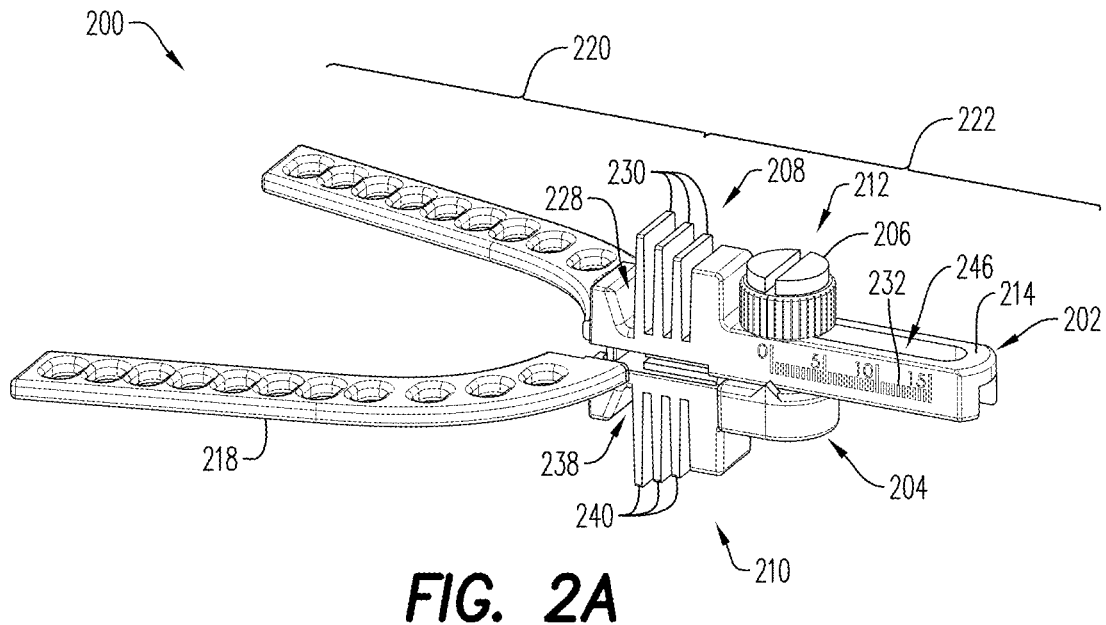
FIG. 2A is a schematic, perspective view of an exemplary jig assembly including an upper jig and a lower jig, according to an embodiment.
Figure 2B:
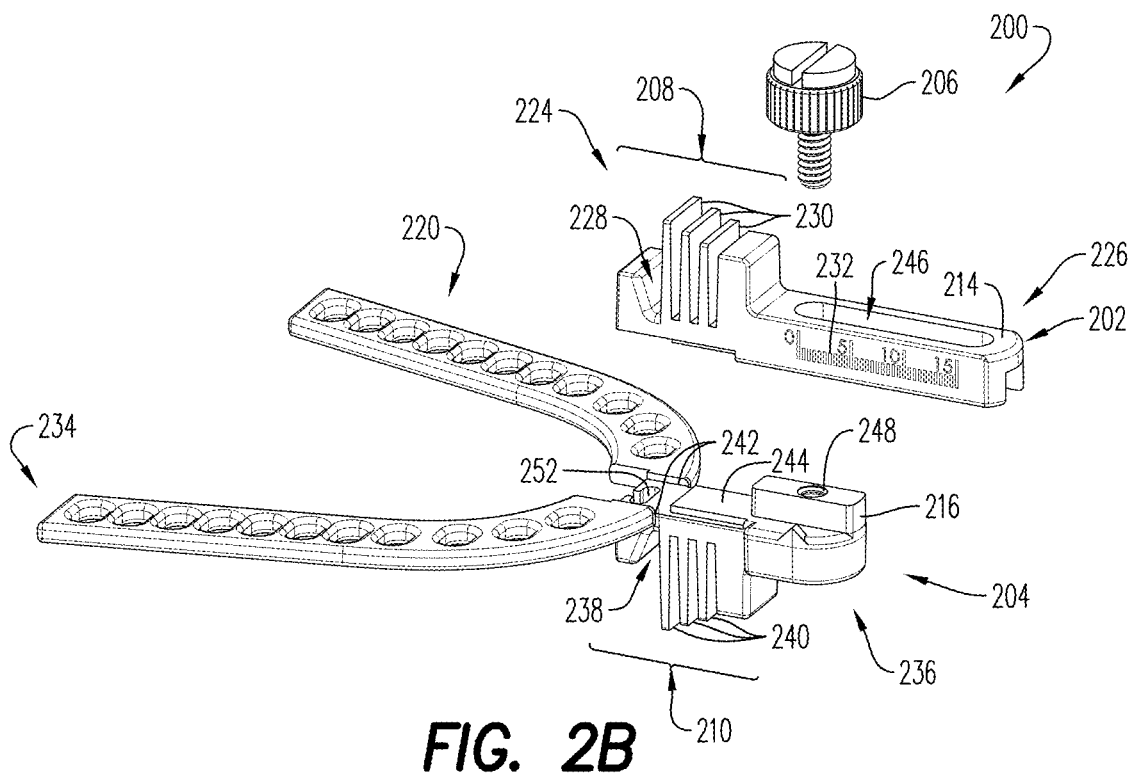
FIG. 2B is a schematic, perspective, exploded view of the jig assembly of FIG. 2A.

For example, FIGS. 2A and 2B schematically illustrate an exemplary jig or jig assembly 200 that may be used, for example, in making an oral appliance (such as, for example, appliance 100 described above). The jig/jig assembly 200 (with optional bitewings 218 removed) may be attached to trays 102, 104 (FIG. 1A) to form a precursor/fabricating assembly 300 (FIG. 3A) for making a provisional oral appliance.

Viewing FIGS. 2A and 2B in detail, the jig or jig assembly 200 includes a first/upper jig part (piece/component/portion/section) 202 and a second/lower jig part (piece/component/portion/section) 204 slidably engaged with one another (i.e., so that the upper jig part 202 and the lower jig part 204 of the jig assembly 200 are able to slide relative to one another). The jig assembly 200 further includes a fastener 206 (e.g., tightening screw/adjustment screw), for example, a nylon thumb screw, for temporarily securing the upper and lower jig parts 202, 204 in relative positions with respect to one another. In some embodiments, the upper and lower jig parts 202, 204 may be formed, for example, from a molded polymeric material (e.g., plastic).

The various components of the jig assembly 200 collectively include and/or define (such that the jig assembly 200 likewise includes) an upper bite block 208 and a lower bite block 210 for respectively receiving the upper and lower teeth of a patient, and an adjustable lock assembly 212 for positioning and securing the upper bite block 208 and lower bite block 210 (and therefore, the user's upper and lower teeth/jaws) in relative positions with respect to one another. The lock assembly 212 includes an adjustment tab (or "tab") 214, an adjustment clamp block (or "adjustment clamp"/ "clamp"/"clamp block") 216 (FIG. 2B), and adjustment screw 206 referenced above. The jig assembly 200 may further include a bitewing 218 for use in making an impression of the patient's teeth and gums, for example, using a fast-setting, self-cure reline material. The upper jig 202 includes the upper bite block 208 and the adjustment tab 214. The lower jig 204 includes the lower bite block 210, the adjustment clamp block 216, and the optional bitewing 218.

As shown in FIGS. 2A and 2B, the adjustment screw 206 extends through the adjustment tab 214 into the top of the adjustment clamp block 216. With the screw loosened, the upper jig 202 including the adjustment tab 214 and the lower jig 204 including the adjustment clamp block 216 are able to slide freely with respect to one another. When the screw 206 is tightened, the sliding motion is impeded and the positions of the upper and lower jigs 202, 204 are fixed with respect to one another.

In use, the jig assembly 200 is intended to be positioned between the upper and lower teeth of a user, such that the upper teeth of the user are positioned within the upper bite block 208 of the upper jig 202 and the lower teeth of the user are positioned within the lower bite block 210 of the lower jig 204. The relative positions of the upper and lower jigs 202, 204 may be adjusted so that the lower jig 204 is offset from the upper jig 202 with the user's lower jaw in a protruded (i.e., forwardly urged) position, for example, in accordance with treatment protocol for sleep apnea. Once the upper and lower jigs 202, 204 are properly positioned and secured using the adjustment screw 206, a three-dimensional scan and/or an impression of the patient's teeth and gums can be made, for example, for use in fabricating an oral appliance for the treatment of sleep apnea.

It will be noted that, in the configuration shown in FIG. 2A (i.e., with the upper and lower bite blocks 208, 210 generally aligned with each other), the jig assembly 200 may be generally described as including a first (e.g., posterior) end or portion 220 for engaging the upper and lower teeth of the patient, and a second (e.g., anterior) end or portion 222 for adjusting and securing the first portion of the jig 200 so that the upper and lower teeth of the patient are arranged and retained in desired positions relative to one another. The posterior portion 220 of the jig assembly 200 includes the upper bite block 208, the lower bite block 210, and the bitewing 218. The anterior portion 222 of the jig assembly 200 includes the adjustable locking assembly 212 (i.e., the adjustment tab 214, the adjustment clamp 216, and the screw 206).

As best seen in FIG. 2B, the upper jig 202 may generally include a posterior end (or portion) 224 and an anterior end (or portion) 226. The upper bite block 208 is positioned along (and at least partially defines) the posterior portion 224 of the upper jig 202. The upper bite block 208 includes a bite groove or slot (e.g., an upper bite groove) 228 for receiving the upper front teeth of the patient. The upper bite block 208 further includes a plurality of removable breakaway tabs 230 (e.g., at 1 mm segmented cuts) positioned adjacent to the upper bite groove 228 to allow the size of the upper bite groove 228 to be adjusted (i.e., increased) to accommodate the size/spacing/geometry of the upper teeth of the patient, if needed. The upper bite block 208 can be made to have any suitable thickness or height as needed, and in some examples, the upper bite block 208 may have a thickness or height of about 3 mm or about 5 mm at its base.

Still viewing FIG. 2B, the adjustment tab 214 is positioned along (and at least partially defines) the anterior portion 226 of the upper jig 202. The adjustment tab 214 may include a plurality of markings 232 (or other visual indicator(s)) at predetermined lengths, for example, at 1 mm lengths, for measuring the proper protrusive position of the patient's lower jaw. In some embodiments, the markings 232 may be colored (e.g., color-coded) (not shown) to simplify the measurement process and thereby potentially improve accuracy and precision in jaw alignment. Additionally or alternatively, in some embodiments (not shown), the jig assembly may include an audible indicator that provides a distinct sound (i.e., click, tone, beep, artificial voice counter, etc.) indicating the degree of movement of the lower jig 204 relative to the upper jig 202 (or vice versa) per each length of movement, for example, about 0.5 mm or about 1 mm. Other possible indicators, for example, tactile indicators, are described above.

Still viewing FIG. 2B, the lower jig 204 may generally include a posterior end (or portion) 234 and an anterior end (or portion) 236. The lower bite block 210 is positioned along (and at least partially defines) the posterior portion 234 of the lower jig 204. The lower bite block 210 includes a bite groove 238 or slot (e.g., a lower bite groove) for receiving the lower front teeth of the patient. The lower bite block 210 further includes a plurality of removable breakaway tabs 240 (e.g., at 1 mm segmented cuts) positioned adjacent to the lower bite groove 238 to allow the size of the lower bite groove 238 to be adjusted (i.e., increased) to accommodate the size/spacing/geometry of the lower teeth of the patient. The lower bite block 210 can be made to have any suitable thickness or height as needed, and in some examples, the lower bite block 210 may have a thickness or height of about 3 mm or about 5 mm at its base.

Additionally, the bitewing 218 (including left and right bitewing portions, not separately labeled) is positioned along (and at least partially defines) the posterior portion 234 of the lower jig 204. A pair of weakened areas or grooves ("breakaway grooves") 242 are positioned along opposite sides of the lower bite block 210 for allowing the dentist to easily bend and snap off the left and right bitewing portions if the bitewing 218 is not needed (e.g., if no impression is being taken). In another embodiment (not shown), the bitewing 218 may be omitted altogether, rather than being removably attached to the lower jig 204.

Still viewing FIG. 2B, the adjustment clamp block 216 is positioned along (and at least partially defines) the anterior portion 236 of the lower jig 204. The adjustment clamp block 216 generally comprises a projection extending upwardly from an upper surface 244 of the lower jig 204 along the anterior end 236 of the lower jig 204. The adjustment clamp block 216 is generally elongate (e.g., rectangular cubic) in shape, and is generally dimensioned to fit within (and slidably engage with) a corresponding adjustment channel 246 extending along and through the adjustment tab 214 of the upper jig 202.

The adjustment clamp block 216 includes a threaded bore or opening 248 for receiving the shaft of the adjustment screw 206. As stated above, with the screw 206 loosened, the upper jig 202 (including the adjustment tab 214) and the lower jig 204 (including the adjustment clamp block 216) are able to slide freely with respect to one another. When the screw 206 is tightened into the threaded bore 248, the sliding motion is impeded and the positions of the upper and lower jigs 202, 204 are fixed with respect to one another.

Figure 3A:
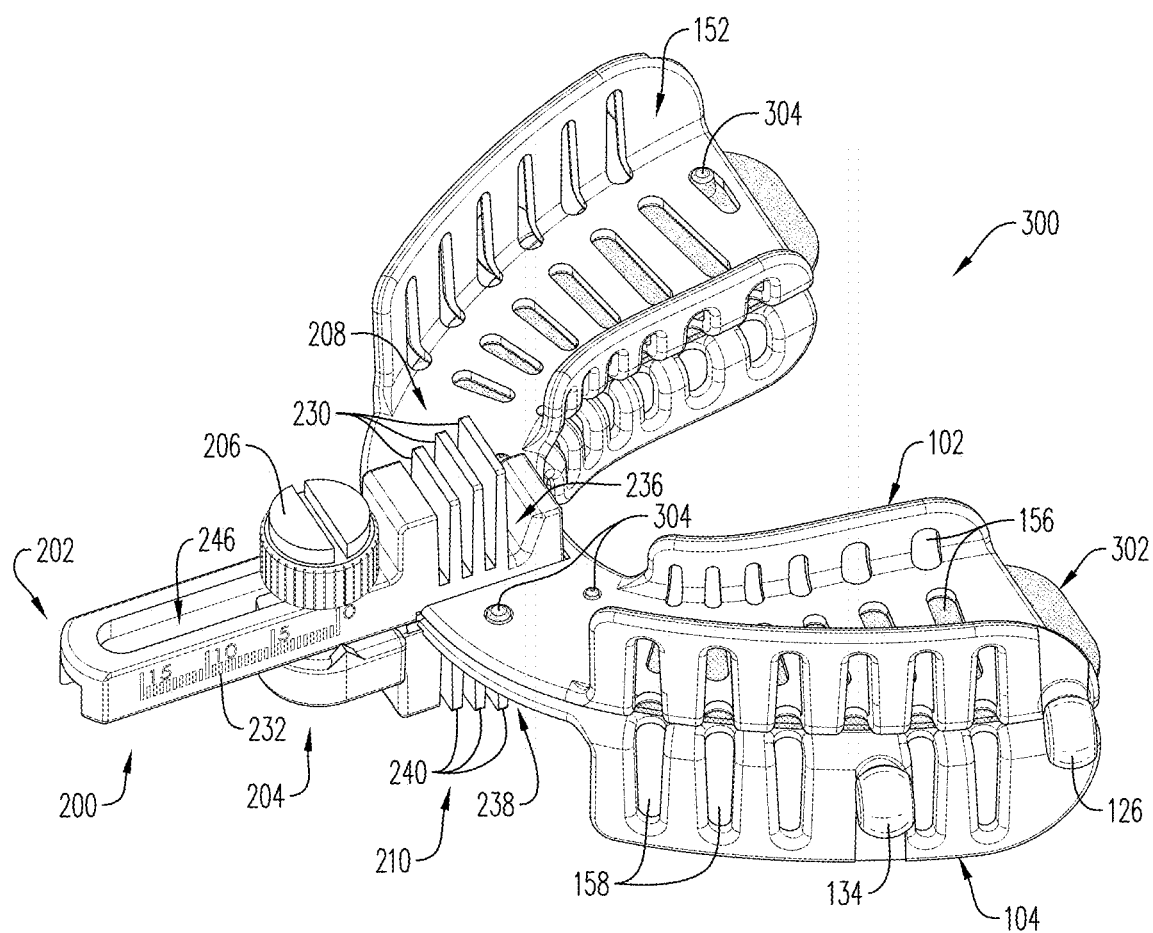
FIG. 3A is a schematic, perspective view of an exemplary precursor fabricating assembly including the jig assembly of FIG. 2A, for making and adjusting the provisional oral appliance of FIG. 1A, according to an embodiment.

As shown in FIG. 3A, the jig assembly 200 (with optional bitewings 218 removed) may be attached to trays 102, 104 (FIGS. 1A and 1C) to form a precursor/fabricating assembly 300 for making and adjusting a provisional oral appliance. FIGS. 3B-3E show various components of the assembly 300 in isolation.

The assembly 300 includes a first (i.e., upper) plate/tray 102 and a second (i.e., lower) plate/tray 104 in an opposed, facing relationship. As discussed in connection with FIG. 1A, the upper tray 102 includes a pair of projections 126 (e.g., flattened balls) extending outwardly from a buccal surface of the upper tray 102 proximate to the anterior end 108 of the upper tray 102 (for eventual mating with sockets 124 of rods 122 to form upper joints 114), and the lower tray 104 includes a pair of projections (e.g., flattened balls) 134 extending outwardly from a buccal surface of the lower tray 104 (for eventual mating with sockets 132 of cylinders 128 to form lower joints 116) (see FIG. 1A).

Figure 3B:
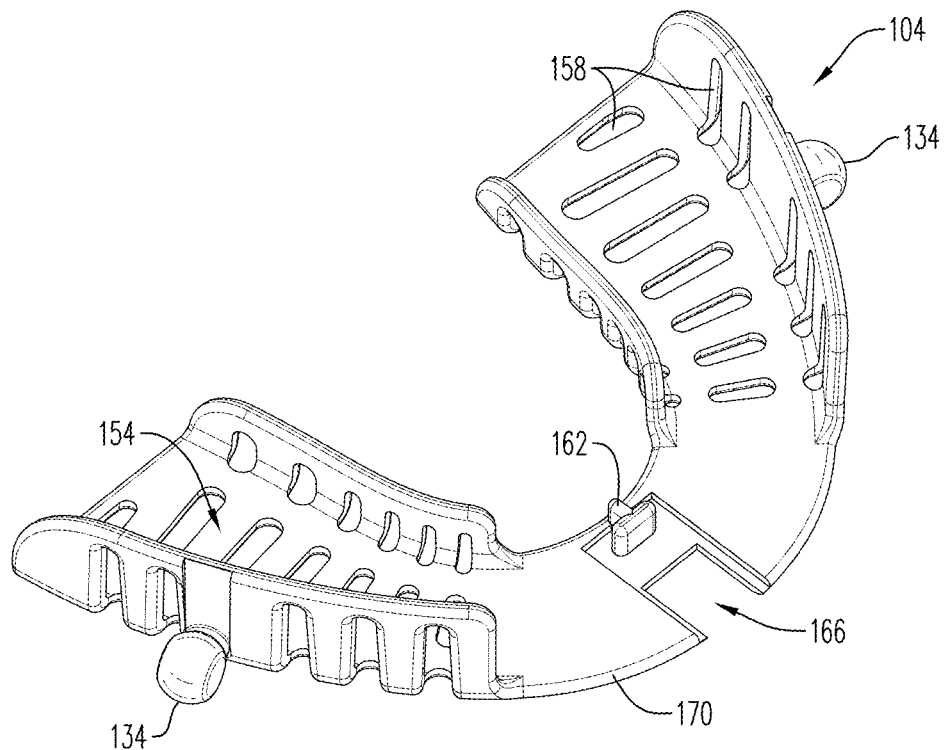
FIG. 3B a schematic, perspective view of the bottom side of the lower tray of the assembly of FIG. 3A, in isolation.

Additionally, as shown in FIG. 3A and FIG. 3B (which shows the bottom tray 104 in an inverted configuration), the upper tray 102 and the lower tray 104 each include a respective channel or cavity 152, 154 for receiving the polymeric material 110 (FIG. 1A), and ultimately, the upper and lower teeth of the patient or user. The upper tray 102 and the lower tray 104 also include a plurality of respective slots 156, 158 (i.e., elongate apertures) for reducing the weight of the appliance and for receiving some of the polymeric material 110, so that the polymeric material adheres better to the trays 102, 104.

The jig assembly 200 generally includes an upper part 202, lower part 204, and fastening screw 206. Additional details and description of the jig 200 assembly are provided above in connection with FIGS. 2A and 2B, and are not repeated here for purposes of brevity.

Figure 3C:
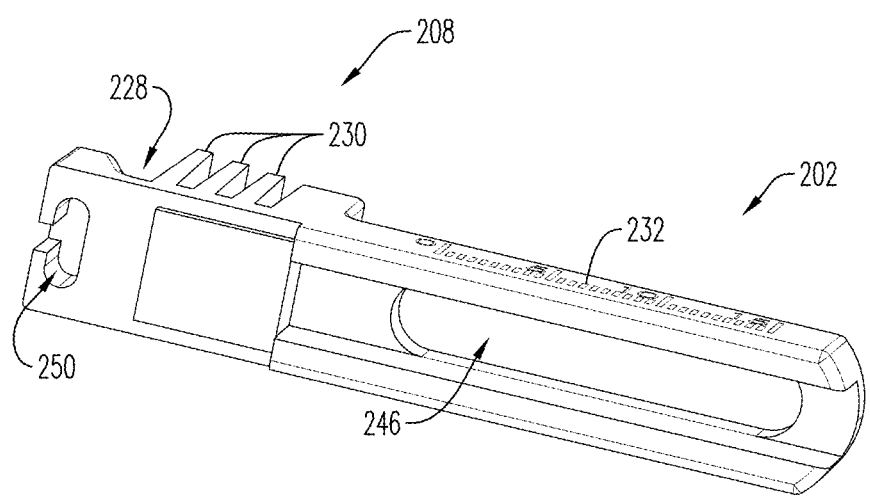
FIG. 3C a schematic, perspective view of the bottom side of the upper jig part of the jig assembly of FIG. 2A used in the assembly of FIG. 3A, in isolation.

As illustrated in, for instance, FIGS. 1A, 2B, 3B, and 3C (of which FIG. 3C shows the lower side of the upper jig 202 in isolation, to attach the jig assembly 200 to the upper and lower trays 102, 104, the upper and lower trays 102, 104 may each be provided with a respective fastening peg 160 (FIG. 1A), 162 (FIG. 3B) for being connected to corresponding respective fastening slots 250 (FIG. 3C), 252 (FIG. 2B) positioned on the side of the respective jig 202, 204 facing the respectively adjacent tray 102, 204. More particularly, the upper jig 202 may be provided with a fastening slot 250 (FIG. 3C) on the lower surface or side of the upper jig 202 for receiving fastening peg 160 (FIG. 1A) positioned on the upper surface or side of the upper tray 202. Likewise, the lower jig 204 may be provided with a fastening slot 252 (FIG. 2B) on the upper surface or side of the lower jig 204 for receiving the fastening peg 162 (FIG. 3B) on the lower surface or side of the lower tray 202. In the illustrated example, pegs 160, 162 and slots 250, 252 are shown as being a rounded T-shape. However, other shaped pegs and slots may be used. Additionally, the upper and lower trays 102, 104 may each also include a notch 164 (FIG. 1A), 166 (FIGS. 1A and 3B) positioned along and defining at least a portion of the anterior edge 168 (FIG. 1A), 170 (FIGS. 1A and 3B of the respective tray 102, 104 for accommodating (i.e., receiving) the bite block 208, 210 (FIG. 3A) of the respective jig 202, 204 to be attached.

Figure 3D:
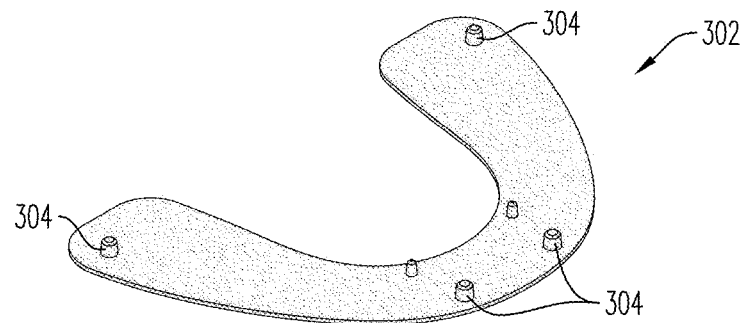
FIG. 3D a schematic, perspective view of a separator plate of the assembly of FIG. 3A, in isolation.

Returning to FIG. 3A and also viewing FIG. 3D, the assembly 300 may further include a separator plate 302 positioned between the first and second trays 102, 104. The separator plate 302 may assist with preventing the first and second trays 102, 104 from becoming adhered to one another during fabrication of the appliance 100. In the embodiment illustrated in FIGS. 3A and 3D, the separator plate 302 has a generally solid configuration with alignment pins 304 (on one or both sides) that are positioned to be received within the slots 156 of the upper tray 102 (and/or slots 158 of the lower tray 204, not shown) to assist with maintaining the separator plate 302 in the desired position during use.

In another aspect, this disclosure is directed to a method of using the jig assembly 200 of FIGS. 2A and 2B, for example, to facilitate the fabrication of a provisional oral sleep appliance, such as appliance 100 described above. More particularly, the jig assembly 200 may be used to form a precursor/fabricating assembly 300, as shown in FIG. 3A to make and adjust a provisional oral sleep appliance, such as appliance 100 (FIG. 1A) described above.

As stated previously, the jig 200 may be provided with attached bitewings 218. If such bitewings 218 are provided, the bitewings 218 may be removed by bending the bitewings along weakened areas 242 (FIG. 2B) prior to use. Alternatively, if no bitewings are provided, the jig assembly 200 may be used as is. If the jig 200 is provided in an assembled condition, the parts may be disassembled by unscrewing the adjustment screw 206 until the upper part 202 and lower part 204 of the jig 200 separate from one another (FIGS. 2A and 2B). Alternatively, if the jig 200 is provided in an unassembled condition, the parts may be used as is.

If the separator plate 302 is being used, it may be positioned between the two trays 102, 104. To attach the jig 200 to the trays 102, 104, the upper jig 202 may be positioned so that the fastening slot 250 (FIG. 3C) on the lower surface or side of the upper jig 202 engages/receives fastening peg 160 (FIG. 1A) extending upwardly from the upper surface or side of the upper tray 102. Likewise, the lower jig 204 may be positioned so that the fastening slot 252 (FIG. 2B) on the upper surface or side of the lower jig 204 engages/receives the fastening peg 162 (FIG. 3B) extending from the lower surface or side of the lower tray 104. The adjustment screw 206 may then be inserted into the threaded opening 248 and turned until the upper and lower jigs 202, 204 are affixed to the trays 102, 104.

The assembly 300 may then be inserted into a patient's mouth so that the upper teeth of the patient are received in the upper tray 102 with the front, upper teeth of the patient seated in the upper bite groove 228, and the lower teeth of the patient are received in the lower tray 104 with the front, lower teeth of the seated in the lower bite groove 238 (best seen in FIGS. 2A and 2B). If needed, one or more of each of the upper and/or lower breakaway tabs 230, 240 may be removed to accommodate the shape/angle of the patient's teeth. Using the markings 232 (or measurements) provided on the adjustment tab 214, the lower jaw of the patient may be adjusted to locate the proper positioning for apneic treatment. For example, the lower jig 204 (and therefore lower tray 104) may be urged forward (i.e., offset) a distance of up to 15 mm (e.g., in up to about 0.5 mm increments), for example, from about 2 mm to about 5 mm, for example, about 3.5 mm. As the lower jig 204 (and lower tray 104) is moved back and forth, the adjustment clamp block 216 slides along the adjustment tab 214. When the desired position is reached, the screw 206 may be tightened into position against the adjustment tab 214.

The upper tray 102 and the lower tray 104, still attached to one another in an offset configuration, may then be removed from the patient's mouth. A fast-setting, self-cure reline material or a dual-cure reline material 110 (FIG. 1A) that is light cured may then be placed within the channel or cavity 152, 154 of the upper and lower trays 102, 104. The trays 102, 104 may then be returned to the patient's mouth, as the patient is instructed to bite down gently onto the trays. As the reline material hardens (typically 2-3 minutes for fast-setting, self-cure reline materials), the shape of the teeth is formed in the reline material. If the dual-cure reline material is used, after it has hardened in the patient's mouth, the trays 102, 104 are removed from the patient's mouth and the dual-cure reline material is light cured. During this time, the presence of the separator plate 302 assists with preventing the trays 102, 104 from adhering to one another. Once the reline material is fully-hardened/set, the trays 102, 104 may be trimmed to remove any excess reline material and to create a smooth surface that will provide a comfortable fit for the patient. The trays 102, 104 may be trimmed using a trimming motor/drill or a laboratory carving knife.

The strut assemblies 112 may then each be adjusted by turning the rod 122 to achieve the desired length/distance between the upper and lower projections 126, 134, as determined by the prior protrusive measurements made above. The strut assemblies 112 may then be mounted onto the trays 102, 104 as described above to form joints 114, 116 (FIG. 1A).

The thumb screw 206 may then be loosened, and the upper and lower trays 102, 104 pried apart (if needed) with a thin, sharp instrument (e.g., a knife or similar device) to remove the separator plate 302, which may be discarded. The upper and lower jig parts 202, 204 may then be removed by loosening screw 206 and disengaging the upper and lower jig parts 202, 204 from the trays 102, 104. Any excess reline material 110 (FIG. 1A) may be shaved off the trays 102, 104. The resulting appliance 100 (FIG. 1A) may then be used for the treatment of sleep apnea, advantageously as described above.

As mentioned above, the jig or jig assembly 200 may also be used for purposes unrelated to the fabrication of an oral appliance. For example, the jig 200 may be used with or without the optional bitewing 118 to position the patient's jaw(s) to take a scan of the patient's teeth. The jig can also be inverted, by interchanging the two bite blocks 208, 210 for either the upper or the lower jaw, in various jaw anatomical and skeletal variations such as a normal proportional upper and lower jaw relations, an over bite where the lower jaw is recessed, or an under bite where the lower jaw is naturally protruded relative to the upper jaw. Additionally or alternatively, if an impression is needed, a fast-setting, self-cure reline material (not shown) may then be deposited on the bitewings 218, and the patient may be instructed to bite down gently onto the bitewing 218. As the reline material or putty hardens (e.g., typically in less than a minute) the shape of the teeth is formed in the reline material. Still other possible uses and variations are contemplated hereby.

If desired, the jig or jig assembly 200 may be provided in combination with the oral appliance trays 102, 104 (and strut assemblies 112) as a "kit". This combination advantageously provides the practitioner a variety of practical tools to draw upon as needed. Alternatively, the jig 200 may be provided separately from the trays 102, 104 and strut assemblies 112. In either case, the present appliance 100 and jig 200 (and intermediate assembly 300) provide significant benefits to the dentist and patient without the expense or inconvenience of having to purchase and sterilize stainless steel tools/components.

Figure 4:
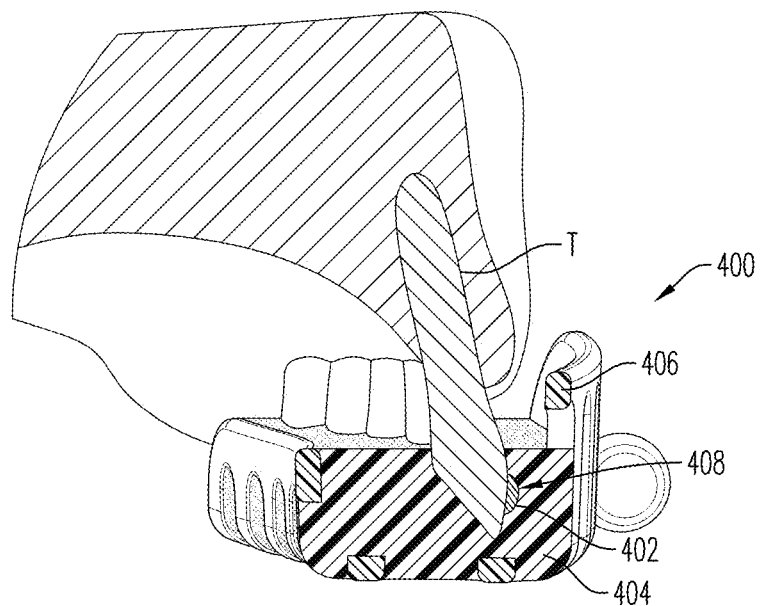
FIG. 4 is a schematic, cross-sectional view of an exemplary oral appliance worn by a user having protrusive buttons mounted to the user's teeth.

In yet another aspect schematically illustrated in FIG. 4, the provisional oral appliance 400 may be further maintained in position using protrusive elements (i.e., small square or rectangular blocks or buttons) 402 adhered to the teeth T of the patient. Specifically, such elements or buttons 402 may be adhered to one or more teeth T (in a manner similar to the brackets of braces) before the making the dental impression of the patient in the reline material (i.e., polymeric material) 404 in the tray 406. When the patient's teeth are pressed into the reline material 404, the reline material 404 flows around and conforms to the geometry of the protrusive elements 402. As a result, the cured reline material 404 and resulting oral appliance 400 includes one or more indentations 408 that correspond to the protrusive element(s) or button(s) on the patient's teeth. The cured reline material 404 is able to deform slightly to allow for the appliance to be inserted, so that the indentations 408 in the reline material 404 can be positioned over the protrusive elements 402 on the user's teeth T. This ability to deform also assists with removal of the appliance 400.

Figure 5A:
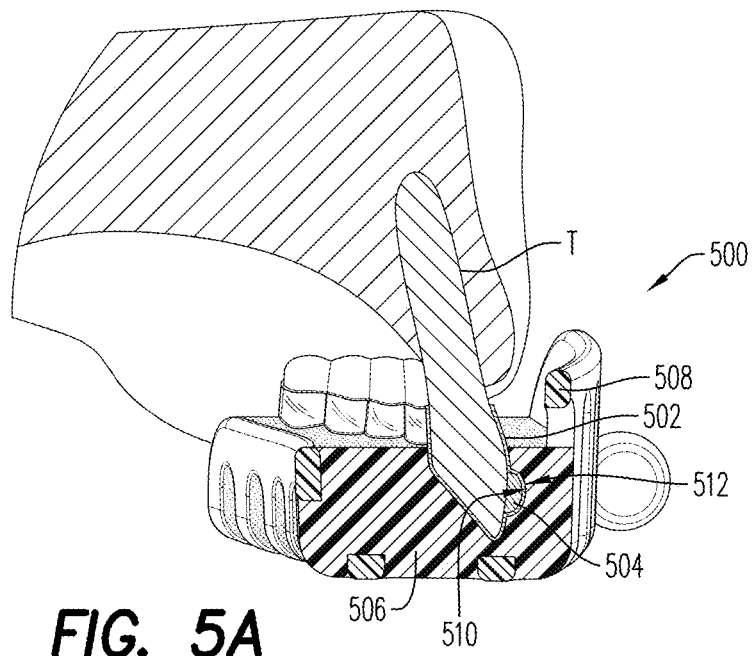
FIG. 5A is a schematic, cross-sectional view of an exemplary oral appliance worn by a user having protrusive buttons mounted to the user's teeth, and wearing an orthodontic aligner.
Figure 5B:
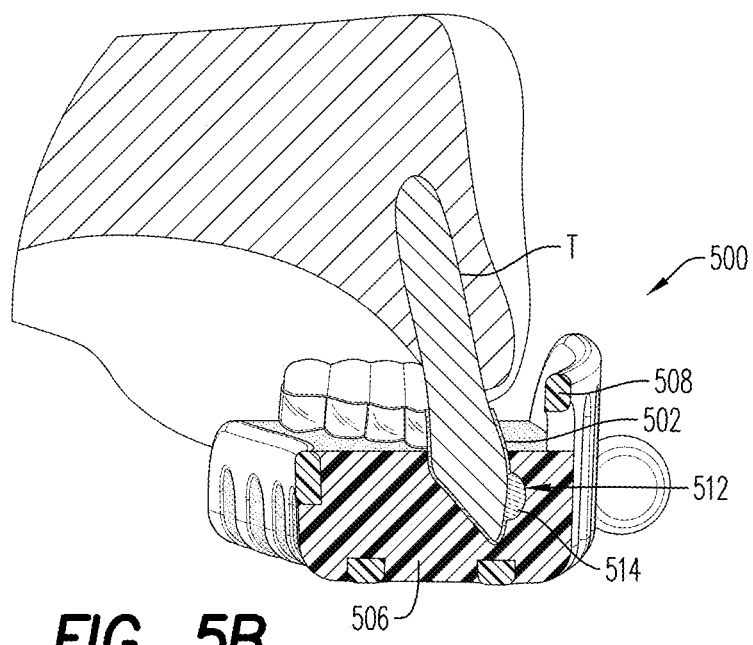
FIG. 5B is a schematic, cross-sectional view of an exemplary oral appliance worn by a user with an orthodontic aligner that includes protrusive geometries on the outer surface of the aligner.

In still another aspect schematically illustrated in FIGS. 5A and 5B, any of the various provisional oral appliances (e.g., appliance 500) described herein or contemplated hereby may be used in connection with one or more orthodontic aligners 502 (e.g., Invisalign-type aligners). With the use of oral appliances for sleep apnea treatment, there may be an unwanted side effect of teeth movement while the patient is in treatment. Additionally or alternatively, there may be a desire for patients to correct their smile line, due to excess spacing or crowding, while oral appliance therapy for sleep apnea is ongoing.

A provisional oral appliance 500 according the present disclosure may be used in conjunction with orthodontic aligner(s) 502 to allow the patient to maintain a protrusive jaw position for treatment of sleep apnea while concurrently undergoing smile line correction. As is understood by those of skill in the art, orthodontic aligners 502 (e.g., such as Invisalign) are fabricated to accommodate the patient's teeth T. The aligners 502 are positioned (i.e., worn) on the teeth and held in place by specifically designed buttons or protrusive elements 504 attached to the patient's teeth. The aligners 502 are changed periodically (e.g., every two weeks). As the aligners are progressively changed, the teeth move into alignment.

To use such aligners 502 with a provisional oral appliance 500 in accordance with the present disclosure, the reline material 506 (i.e., polymeric material) in the tray 508 of the oral appliance may be contoured to accommodate the shape of the orthodontic aligner 502. More particularly, when an orthodontic aligner is fabricated (e.g., typically using a vacuum forming process), protrusions 510 may be formed in the orthodontic aligner 500 in the areas of the attachment buttons 504. When the patient's teeth are pressed into the reline material (wearing the orthodontic aligner), the reline material 506 flows around and conforms to the geometry of the orthodontic aligner 502, including the protrusions 510 formed in the orthodontic aligner around the attachments/buttons on the patient's teeth, as shown in FIG. 5A. As a result, the reline material 506 of the oral appliance 500 is formed to include one or more indentations 512 that correspond to the protrusive element(s) or button(s) 504 on the patient's teeth and the protrusions 510 in the orthodontic aligner 502. The engagement between the protrusion 510 in the aligner 502 and corresponding indentation 512 in the reline material 506 creates the interference necessary to retain the provisional oral appliance 500 to the orthodontic aligner 502.

Similar to that discussed above in connection with FIG. 4, when the patient places the oral appliance 500 over the orthodontic aligner, the oral appliance trays 508 and the reline material 506 will deform just enough to slide over the orthodontic aligner protrusions 510. Since the protrusions 510 on the outside of the orthodontic aligner 502 are produced utilizing a vacuum forming process, the protrusions 510 will be smoother than the original button 504 geometry. As a result, the retention between the reline material 506 and the orthodontic aligner 500 will be less than the retention between the orthodontic aligner 502 and the patient's teeth T. Therefore, the patient can remove the oral appliance 500 without the orthodontic aligner 502 becoming dislodged, leaving the orthodontic aligner 502 in place on the teeth T.

In this and other embodiments, the dentist feels the need to have more retention between the reline material 506 and the orthodontic aligner 502, the dentist can request additional protrusion geometries 514 (i.e., thicker areas/projections) be added along the outside surface of the orthodontic aligner 502, as schematically illustrated in FIG. 5B. Such additional protrusions 514 may create additional interference with the reline material 506 in the tray 508 and assist with retaining the oral appliance 500 in position.

In one variation, the appropriate protrusive measurements for the provisional oral appliance will have already been determined prior to the placement of the provisional appliance over the orthodontic aligner. Upon completion of the orthodontic treatment with that specific aligner and when it is indicated to progress to the next aligner, the reline material as well as the old aligner may be removed, the new aligner placed over the teeth, and new reline material placed into the oral appliance. This process may be performed by a dentist, for example, every two weeks, as the aligners are replaced with new ones. This technique may be used, for example, for smile line correction for patients who desire an improvement in the alignment of their teeth, while they undergo treatment with their oral appliance.

In another variation (not shown), to avoid replacement of the reline material of the oral appliance during orthodontic treatment, the reline material may only be placed within the oral appliance to cover the area of the aligner that is overlying the teeth that are not involved in the orthodontic movement (i.e., avoiding the area that is being treated with the orthodontic aligner). To accomplish this and increase the retention of the provisional oral appliance reline material, the aligner may include retention extensions (i.e., additional protrusions, such as those described above in connection with FIG. 5B) extending outwardly from the outer surface of the aligner. These retention extensions and corresponding indentations in the reline material engage one another to assist with maintaining the oral appliance in the desired position.

In still another aspect, any of the various concepts described herein or contemplated hereby may be used in conjunction with a custom oral appliance (COA), rather than a provisional oral appliance. Thus, for example, a custom oral appliance may include strut assemblies similar to those described above (e.g., strut assemblies 112). Such assemblies may be made of a moldable polymeric material (as described above), stainless steel, or otherwise. A custom oral appliance may also be used with protrusive elements 402, 504 and/or aligners 502 described above.

For example, a custom oral appliance may be fabricated by either digitally scanning the patient's jaw/dentition or taking conventional impression molds. A clear retainer type aligner may initially be fabricated on the dentition to help maintain the position and alignment of the mature dentition during oral appliance sleep therapy. If the patient is interested in performing smile line orthodontic treatment either at the initiation of the oral sleep therapy or while they are being treated with the COA or POA, Invisalign type trays can be fabricated and changed every two weeks while continuing with their prescribed oral sleep therapy.

After scanning or using impression material to capture the dentition, the laboratory will fabricate custom oral appliance trays (e.g., top and bottom trays) that may include a cured and/or adhered lining that can be inserted over the already fabricated clear aligner or Invisalign type trays.

The present disclosure, in various embodiments, configurations and aspects, includes components, methods, processes, systems and/or apparatus substantially developed as depicted and described herein, including various embodiments, sub-combinations, and subsets thereof. Those of skill in the art will understand how to make and use the present disclosure after understanding the present disclosure. The present disclosure, in various embodiments, configurations and aspects, includes providing devices and processes in the absence of items not depicted and/or described herein or in various embodiments, configurations, or aspects hereof, including in the absence of such items as may have been used in previous devices or processes, e.g., for improving performance, achieving ease and/or reducing cost of implementation.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C", and "A, B, and/or C" means A alone, B alone, C alone, A and B together, A and C together, B and C together, or A, B and C together.

In this specification and the claims that follow, reference will be made to a number of terms that have the following meanings. The terms "a" (or "an") and "the" refer to one or more of that entity, thereby including plural referents unless the context clearly dictates otherwise. As such, the terms "a" (or "an"), "one or more", and "at least one" can be used interchangeably herein. Furthermore, references to "one embodiment", "some embodiments", "an embodiment", and the like are not intended to be interpreted as excluding the existence of additional embodiments that also incorporate the recited features. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Terms such as "first", "second", "upper", "lower", etc. are used to identify one element from another, and unless otherwise specified are not meant to refer to a particular order or number of elements. All directional references (e.g., "upper", "lower", "upward", "downward", "left", "right", "leftward", "rightward", "top", "bottom", "above", "below", "vertical", "horizontal", "clockwise", and "counterclockwise") are used only for identification purposes to aid the reader's understanding of the various embodiments of the present invention, and do not create limitations, particularly as to the position, orientation, or use of the invention unless specifically set forth in the claims.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

As used in the claims, the word "comprises" and its grammatical variants logically also subtend and include phrases of varying and differing extent such as for example, but not limited thereto, "consisting essentially of" and "consisting of" Where necessary, ranges have been supplied, and those ranges are inclusive of all sub-ranges therebetween. It is to be expected that variations in these ranges will suggest themselves to a practitioner having ordinary skill in the art and, where not already dedicated to the public, the appended claims should cover those variations.

The terms "determine", "calculate", "compute" and variations thereof, as used herein, are used interchangeably and include any type of methodology, process, mathematical operation, or technique.

The foregoing discussion of the present disclosure has been presented for purposes of illustration and description. The foregoing is not intended to limit the present disclosure to the form or forms disclosed herein. In the foregoing Detailed Description for example, various features of the present disclosure are grouped together in one or more embodiments, configurations, or aspects for the purpose of streamlining the disclosure. The features of the embodiments, configurations, or aspects of the present disclosure may be combined in alternate embodiments, configurations, or aspects other than those discussed above. This method of disclosure is not to be interpreted as reflecting an intention that the present disclosure requires more features than are expressly recited in each claim. Rather, as the following claims reflect, the claimed features lie in less than all features of a single foregoing disclosed embodiment, configuration, or aspect. Thus, the following claims are hereby incorporated into this Detailed Description, with each claim standing on its own as a separate embodiment of the present disclosure.

Advances in science and technology may make equivalents and substitutions possible that are not now contemplated by reason of the imprecision of language; these variations should be covered by the appended claims. This written description uses examples to disclose the method, machine and computer-readable medium, including the best mode, and also to enable any person of ordinary skill in the art to practice these, including making and using any devices or systems and performing any incorporated methods. The patentable scope thereof is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal language of the claims.

What is claimed is:

1. A jig assembly for positioning upper and lower teeth of a patient relative to one another, the jig assembly comprising:
    an upper jig including an upper bite block for receiving the upper teeth of the patient;
    a lower jig including a lower bite block for receiving the lower teeth of the patient; and
    an adjustable lock assembly comprising:
        an adjustment tab comprising an adjustment channel, wherein the adjustment channel extends through the adjustment tab;
        an adjustment clamp block; and
        a fastener, wherein
    the adjustment clamp block fits within the adjustment channel,
    the adjustment clamp block comprises a threaded bore configured for receiving the fastener,
    the adjustment clamp block and the adjustment tab are configured to engage one another so that the upper jig is in sliding engagement with the lower jig, and
    the fastener is configured for securing each of the upper jig and the lower jig in a fixed position relative to one another.

2. The jig assembly of claim 1, wherein the lower jig is secured in a fixed position relative to the upper jig such that the lower teeth of the patient are urged forwardly relative to the upper teeth of the patient.

3. The jig assembly of claim 1, wherein the upper bite block and the lower bite block each comprise:
    a respective bite groove; and
    a plurality of breakaway tabs.

4. The jig assembly of claim 1, wherein the lower jig further comprises a detachable bitewing.

5. The jig assembly of claim 1, in combination with an upper tray and a lower tray for receiving the upper teeth and lower teeth of the patient, the upper tray and the lower tray each having a posterior end, an anterior end, and a pair of opposed sides, wherein:
    the adjustment tab extends from the anterior end of the upper tray; and
    the adjustment clamp block extends from the anterior end of the lower tray.

6. The combination of claim 5, wherein:
    the upper jig includes a receiving slot for mating with a fastening peg extending upwardly from the upper tray; and
    the lower jig includes a receiving slot for mating with a fastening peg extending downwardly from the lower tray.

7. The combination of claim 6, wherein the upper tray and the lower tray each comprise:
    a notch extending inwardly from a respective anterior edge of the upper tray and the lower tray, wherein
    the notch of the upper tray is configured for receiving the upper bite block of the upper jig, and
    the notch of the lower tray is for receiving the lower bite block of the lower jig.

8. A jig assembly for positioning upper teeth and lower teeth of a patient, the jig assembly comprising:
    a first jig comprising a first bite block configured to receive one of the upper teeth and the lower teeth, and an adjustment tab extending from the first bite block;
    a second jig coupled to the first jig, the second jig comprising a second bite block configured to receive the other of the upper teeth and the lower teeth, and an adjustment clamp block extending from the second bite block; and
    a fastener, wherein
        the adjustment tab comprises an adjustment channel, wherein the adjustment channel extends through the adjustment tab,
        the adjustment clamp block fits within the adjustment channel, and
        the fastener is configured for securing each of the first jig and the second jig in a fixed position relative to one another such that the first jig and the second jig are switchable between a first configuration in which the first jig is slidable relative to the second jig in a first direction and a second configuration in which the first jig and the second jig are fixed relative to each other by the fastener in the first direction.

9. The jig assembly of claim 8, further comprising:
a plurality of bitewings extending from the first jig or the second jig.

10. The jig assembly of claim 9, wherein each bitewing of the plurality of bitewings is detachable from the first jig or the second jig.

11. The jig assembly of claim 8, wherein:
each of the first bite block and the second bite block comprise a bite groove and one or more removable tabs; and
the one or more removable tabs are removable so as to vary a size of the bite groove in the first direction.

12. The jig assembly of claim 8, wherein the adjustment clamp block comprises a threaded bore, and the fastener is coupled to a threaded bore formed in the adjustment clamp block to couple the first jig to the second jig.

13. The jig assembly of claim 12, wherein:
the fastener comprises a head and a threaded screw extending from the head in a second direction perpendicular to the first direction;
the adjustment tab comprises an adjustment groove extending through the adjustment tab, the adjustment groove being configured to receive the threaded screw therethrough and having a length in the first direction that is larger than a width of the threaded screw in the first direction; and
the adjustment clamp comprises a threaded bore configured to receive the threaded screw.

14. The jig assembly of claim 8, further comprising:
a first tray coupled to the first jig; and
a second tray coupled to the second jig.

15. The jig assembly of claim 14, further comprising:
a separator provided between the first tray and the second tray.

16. The jig assembly of claim 14, wherein:
the first jig comprises a first slot;
the first tray comprises a first peg inserted into the first slot;
the second jig comprises a second slot; and
the second tray comprises a second peg inserted in to the second slot.

17. The jig assembly of claim 8, further comprising:
a plurality of markings provided on one or both of the first jig and the second jig,
wherein the plurality of markings is configured to indicate a relative displacement between the first jig and the second jig in the first direction.

18. The jig assembly of claim 17, wherein
the plurality of markings is provided on the adjustment tab.

19. A jig assembly for positioning upper and lower teeth of a patient relative to one another, the jig assembly comprising:
an upper jig including an upper bite block for receiving the upper teeth of the patient, wherein the upper bite block includes a bite groove for receiving the upper front teeth of the patient and a plurality of upper breakaway tabs positioned adjacent to the upper bite groove;
a lower jig including a lower bite block for receiving the lower teeth of the patient, wherein the lower bite block includes a bite groove for receiving the lower front teeth of the patient and a plurality of lower breakaway tabs positioned adjacent to the lower bite groove, wherein
one or more of each upper breakaway tab of the plurality of upper breakaway tabs and each lower breakaway tab of the plurality of lower breakaway tabs are configured to be removable so as to accommodate at least one of the patient's upper teeth and lower teeth.

20. The jig assembly of claim 19, wherein the lower jig further comprises a detachable bitewing.

* * * * *